(12) United States Patent
Simionescu et al.

(10) Patent No.: US 9,283,241 B2
(45) Date of Patent: Mar. 15, 2016

(54) TREATMENT TO RENDER IMPLANTS RESISTANT TO DIABETES

(71) Applicant: Clemson University, Clemson, SC (US)

(72) Inventors: Agneta Simionescu, Pendleton, SC (US); Dan Simionescu, Pendleton, SC (US); James Chow, Columbia, SC (US)

(73) Assignee: Clemson University, Clemson, SC (US)

( * ) Notice: Subject to any disclaimer, the term of this patent is extended or adjusted under 35 U.S.C. 154(b) by 70 days.

(21) Appl. No.: 13/938,275

(22) Filed: Jul. 10, 2013

(65) Prior Publication Data

US 2014/0018909 A1  Jan. 16, 2014

Related U.S. Application Data

(60) Provisional application No. 61/669,752, filed on Jul. 10, 2012.

(51) Int. Cl.

| *A61F 2/06* | (2013.01) |
| *A61K 31/7024* | (2006.01) |
| *A61K 31/7034* | (2006.01) |
| *A61F 2/24* | (2006.01) |
| *A61F 2/82* | (2013.01) |
| *A61L 27/22* | (2006.01) |
| *A61L 27/24* | (2006.01) |

(Continued)

(52) U.S. Cl.
CPC ............... *A61K 31/7034* (2013.01); *A61F 2/24* (2013.01); *A61F 2/82* (2013.01); *A61K 31/7024* (2013.01); *A61K 31/7032* (2013.01); *A61L 27/227* (2013.01); *A61L 27/24* (2013.01); *A61L 27/3633* (2013.01); *A61L 27/3683* (2013.01); *A61L 27/3687* (2013.01); *A61L 27/50* (2013.01); *A61L 27/507* (2013.01); *A61L 27/54* (2013.01); *A61L 2300/216* (2013.01); *A61L 2400/18* (2013.01); *A61L 2430/20* (2013.01)

(58) Field of Classification Search
CPC ........................ A61F 2/24; A61F 2/82; A61K 31/7024–31/7034
USPC .............................................. 623/23.7–23.76
See application file for complete search history.

(56) References Cited

U.S. PATENT DOCUMENTS

| 4,992,264 A | 2/1991 | Diot et al. |
| 5,015,677 A | 5/1991 | Benedict et al. |

(Continued)

OTHER PUBLICATIONS

Article—*Aneurysm of the Rabbit Common Carotid Artery Induced by Periarterial Application of Calcium Chloride In Vivo*, Gertz et al., J. Clin. Invest., vol. 81, Mar. 1988, pp. 649-656.

(Continued)

*Primary Examiner* — Suzette J Gherbi
(74) *Attorney, Agent, or Firm* — Dority & Manning, P.A.

(57) ABSTRACT

Disclosed is a medical device treated with a phenolic compound and a process for treating a device with the phenolic compound. For example, a collagen or elastin-based scaffold can be treated with pentagalloyl glucose (PGG). The treated scaffold can become resistant to glycoxidative stress associated with advanced glycation end products (AGEs) that are present in a hyperglycemic environments associated with diabetes mellitus. The treated scaffold can exhibit a reduced increase in stiffness as compared to an untreated scaffold. The treated scaffold can also exhibit reduced inflammation without negatively affecting the ability of the scaffold to remodel in vivo.

14 Claims, 22 Drawing Sheets
(8 of 22 Drawing Sheet(s) Filed in Color)

(51) Int. Cl.
*A61L 27/36* (2006.01)
*A61L 27/50* (2006.01)
*A61L 27/54* (2006.01)
*A61K 31/7032* (2006.01)

(56) References Cited

U.S. PATENT DOCUMENTS

| | | | |
|---|---|---|---|
| 5,720,950 A | 2/1998 | Poiani et al. | |
| 5,750,150 A | 5/1998 | Okazaki et al. | |
| 5,876,744 A | 3/1999 | Della Valle et al. | |
| 5,968,500 A | 10/1999 | Robinson | |
| 5,972,999 A | 10/1999 | Murad | |
| 6,146,616 A | 11/2000 | Msika et al. | |
| 6,235,294 B1 | 5/2001 | Perrier et al. | |
| 6,239,114 B1 | 5/2001 | Guthrie et al. | |
| 6,254,898 B1 | 7/2001 | Bragaglia | |
| 6,391,538 B1* | 5/2002 | Vyavahare et al. | 435/1.1 |
| 6,432,922 B1 | 8/2002 | Brunck et al. | |
| 6,437,004 B1 | 8/2002 | Perricone | |
| 6,444,234 B1 | 9/2002 | Kirby et al. | |
| 6,469,053 B1 | 10/2002 | Romanczyk, Jr. et al. | |
| 6,471,973 B1 | 10/2002 | Perrier et al. | |
| 6,517,824 B1 | 2/2003 | Kohn et al. | |
| 6,576,613 B1 | 6/2003 | Brunck et al. | |
| 6,586,405 B2 | 7/2003 | Semple et al. | |
| 6,610,320 B2 | 8/2003 | Schmitz et al. | |
| 6,630,163 B1 | 10/2003 | Murad | |
| 6,676,977 B2 | 1/2004 | Murad | |
| 6,747,059 B1 | 6/2004 | Romanczyk, Jr. et al. | |
| 6,787,152 B2 | 9/2004 | Kirby et al. | |
| 6,800,292 B1 | 10/2004 | Murad | |
| 6,830,577 B2 | 12/2004 | Nash et al. | |
| 6,867,188 B2 | 3/2005 | Qvist et al. | |
| 6,927,205 B2 | 8/2005 | Patt | |
| 6,927,206 B2 | 8/2005 | Patt | |
| 6,929,626 B2 | 8/2005 | DiCarlo et al. | |
| 7,022,674 B2* | 4/2006 | DeFelippis et al. | 514/5.9 |
| 7,252,834 B2 | 8/2007 | Vyavahare et al. | |
| 7,368,125 B2 | 5/2008 | Nathan | |
| 7,910,102 B2* | 3/2011 | Sullivan et al. | 424/134.1 |
| 8,496,911 B2* | 7/2013 | Weldon et al. | 424/9.1 |
| 2002/0172706 A1* | 11/2002 | Vyavahare et al. | 424/423 |
| 2003/0171287 A1 | 9/2003 | Morishita et al. | |
| 2005/0079202 A1 | 4/2005 | Chen et al. | |
| 2008/0288057 A1* | 11/2008 | Carpenter et al. | 623/1.42 |
| 2009/0226528 A1* | 9/2009 | Czech et al. | 424/491 |
| 2010/0331880 A1* | 12/2010 | Stopek | 606/219 |
| 2012/0195879 A1* | 8/2012 | Walker et al. | 424/130.1 |
| 2012/0231079 A1* | 9/2012 | Gupta et al. | 424/486 |
| 2013/0023474 A1* | 1/2013 | Ling et al. | 514/9.1 |
| 2013/0295081 A1* | 11/2013 | Guelcher et al. | 424/130.1 |
| 2014/0199412 A1* | 7/2014 | Huang et al. | 424/616 |
| 2014/0363564 A1* | 12/2014 | Rule et al. | 427/2.31 |

OTHER PUBLICATIONS

Book—*Antinutrients and Phytochemicals in Foods (Methods for determination of condensed and hydrolysable tannins)*, Hagerman et al., Shahadi, F., Ed., Washington, DC, American Chemical Society, 1997, pp. 209-222.

Article—*Design and Testing of a Pulsatile Conditioning System for Dynamic Endothelialization of Polyphenol-Stabilized Tissue Engineered Heart Valves*, Sierad et al., Cardiovasc. Eng. Technol., Jun. 2010, 21 pages.

Article—*Elastin fragments drive disease progression in a murine model of emphysema*, Houghton et al., The Journal of Clinical Investigation, vol. 116, No. 3, Mar. 2006, pp. 753-759.

Article—*Elastin stabilization in cardiovascular implants: improved resistance to enzymatic degradation by treatment with tannic acid*, Isenburg et al., Biomaterials 25, 2004, pp. 3293-3302.

Article—*Inflammation and Matrix Metalloproteinases in the Enlarging Abdominal Aortic Aneurysm*, Freestone, et al., Arteriosclerosis, Thrombosis, and Vascular Biology, vol. 15, 1995, pp. 1145-1151.

Article—*Influence of Hypercholesterolemia and Adventitial Inflammation on the Development of Aortic Aneurysm in Rabbits*, Freestone, et al., Arteriosclerosis, Thrombosis, and Vascular Biology, vol. 17, 1997, pp. 10-17.

Article—*Interstitial chemotherapy with drug polymer implants for the treatment of recurrent gliomas*, Brem et al., Journal of Neurosurgery, vol. 74, No. 3, Mar. 1991, pp. 441-446.

Article—*Pharmaceutical Salts*, Berge et al., Journal of Pharmaceutical Sciences, vol. 66, No. 1, Jan. 1977, pp. 1-19.

Article—*Polyphenol-Stabilized Tubular Elastin Scaffolds for Tissue Engineered Vascular Grafts*, Chuang et al., Tissue Engineering: Part A, vol. 15, No. 10, 2009, pp. 2837-2851.

Article—*Provocation of experimental aortic inflammation and dilation by inflammatory mediators and* Chlamydia pneumoniae, Tambiah et al., British Journal of Surgery, vol. 88, 2001, pp. 935-940.

Article—*Tannic acid treatment enhances biostability and reduces calcification of glutaraldehyde fixed aortic wall*, Isenburg et al., Biomaterials 26, 2005, pp. 1237-1245.

\* cited by examiner

TREATMENT TO RENDER IMPLANTS RESISTANT TO DIABETES

CROSS REFERENCE TO RELATED APPLICATIONS

This application claims filing benefit of previously filed U.S. Provisional Patent Application Ser. No. 61/669,752 having a filing date of Jul. 10, 2012, incorporated herein by reference in its entirety.

FEDERALLY SPONSORED RESEARCH AND DEVELOPMENT

This invention was made with government support under grant number R21 EB009835 awarded by the National Institute of Health. The government has certain rights in the invention.

BACKGROUND OF THE INVENTION

It is estimated that over 8 percent of the world population is affected with diabetes mellitus, including about 26 million people in the United States alone. Diabetes mellitus increases the risk of problems related to the body's vascular system. Macrovascular complications can lead to accelerated atherosclerosis, coronary heart disease, and peripheral arterial disease. In addition, microvascular complications can lead to retinopathy, nephropathy, and neuropathy. Studies show that diabetes mellitus increases the risk of the occurrence of cardiovascular disease, and about 68 percent of the people affected with diabetes mellitus die due to cardiovascular disease. Health care costs associated with cardiovascular diseases total close to $15 billion dollars. Because of the high prevalence of cardiovascular disease in patients with diabetes mellitus, this particular patient population must undergo a greater number of cardiovascular surgeries to repair or replace key components of the cardiovascular system, such as heart valves and blood vessels. These surgeries often result in more complications for diabetic patients than other patient populations.

One of the complications associated with cardiovascular repair or replacement surgeries in patients with diabetes mellitus is that in diabetic environments, hyperglycemic conditions can result in the irreversible oxidation of lipids, proteins, and nucleic acids, which results in the formation of advanced glycation end products (AGEs). The formation of AGEs often results in endothelial dysfunction, accelerated atherosclerosis, inflammation, and calcification. Other complications are associated with inadequate biomechanical function of the aortic valve due to valvular stenosis and calcification.

In addition to AGE formation, glycoxidation in a diabetic environment is also directly influenced by oxidative stress. This oxidative stress can be induced by the formation of reactive oxygen species (ROS), which are free radicals. While not fully understood, it is believed that ROS formation is likely due to a combination of alterations of intracellular proteins, particularly in the mitochondria, and inflammatory cell (i.e., neutrophils and macrophages) recruitment. Many AGE formations, discussed above, depend on the presence of ROS, and further ROS may be produced by AGE formation.

Still other complications related to diabetes mellitus include an adverse effect on wound healing and matrix remodeling, which are integral aspects of matrix scaffold-based tissue engineering, which is being used to treat pathological complications due to cardiovascular disease. Tissue engineered scaffolds have been derived from xenogenic extracellular matrix (ECM) because of its ideal natural, three-dimensional architecture and its ability to remodel and become quickly and completely degraded. However, ECM scaffolds that are implanted into diabetic patients do not behave the same as those implanted into non-diabetic patients, and the ECM scaffolds often show increased stiffness and inflammation, which can be attributed to the formation of AGEs in a hyperglycemic and oxidative environment, resulting in irreversible crosslinking, impaired remodeling and regeneration, and fibrosis.

As such, there is a need for an improved cardiovascular implant that can be used in patients with diabetes mellitus that is not as susceptible to the damaging effects of AGEs. In particular, treating implantable devices or scaffolds with a phenolic compound could provide a means of mitigating diabetes-related complications associated with implantable devices due to a hyperglycemic environment and glycoxidation. Phenolic compounds are a diverse group of materials that have been recognized for use in a wide variety of applications. For instance, they naturally occur in many plants, and are often a component of the human diet. Phenolic compounds have been examined in depth for their efficacy as free radical scavengers and neutralizers, for instance in topical skin applications and in food supplements. Phenolic compounds are also believed to prevent the cross-linking of cell membranes found in certain inflammatory conditions and are believed to affect the expressions of specific genes due to their modulation of free radicals and other oxidative species.

SUMMARY OF THE INVENTION

In one embodiment, the present disclosure is directed to a method for rendering an implant resistant to diabetes. The method comprises applying a phenolic compound to the implant, wherein the phenolic compound comprises a hydrophobic core and at least one phenolic group joined to the hydrophobic core.

In another embodiment, the method can further comprise implanting the implant into a subject. In certain embodiments, the implant can be implanted into a diabetic environment. The phenolic compound can inhibit production of advanced glycation end products and can also inhibit degradation of the implant. In one embodiment, the phenolic compound can be a tannin. For instance, the phenolic compound can be tannic acid or a derivative of tannic acid. More specifically, in some embodiments, the derivative of tannic acid can be pentagalloylglucose. The phenolic compound can be applied to the implant by immersing the implant in a treatment solution, where the phenolic compound is present in the treatment solution at a concentration ranging from about 0.0001 w/v % to about 10 w/v %.

In still another embodiment, the present disclosure is directed to a composition for rendering an implant resistant to diabetes. The composition comprises between about 0.0001 w/v % and about 10 w/v % of a phenolic compound, the phenolic compound comprising a hydrophobic core and at least one phenolic group joined to the hydrophobic core; and a carrier. The composition has a pH between about 4 and about 9.

In one embodiment, the phenolic compound in the composition can be a tannin. For instance, the phenolic compound can be tannic acid or a derivative of tannic acid. More specifically, in some embodiments, the derivative of tannic acid can be pentagalloylglucose. In certain embodiments, the phenolic compound can include one or more double bonds. In other embodiments, the composition can have a pH of between about 5.5 and about 7.4. In yet other embodiments, the composition can include less than about 5% free gallic acid residue.

In one more embodiment, the present disclosure is directed to an implant comprising a scaffold treated with a solution comprising about 0.0001 w/v % and about 10 w/v % of a phenolic compound, the phenolic compound comprising a hydrophobic core and at least one phenolic group joined to the hydrophobic core. The implant can be a collagen-based scaffold or an elastin-based scaffold. In one embodiment, the implant can be a replacement heart valve, while in another embodiment, the implant can be a replacement blood vessel, such as a decellularized artery in one particular embodiment. Moreover, the phenolic compound can be a tannin, such as tannic acid or a derivative thereof. For instance, the phenolic compound can be pentagalloylglucose. Further, the phenolic compound can comprise one or more double bonds.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
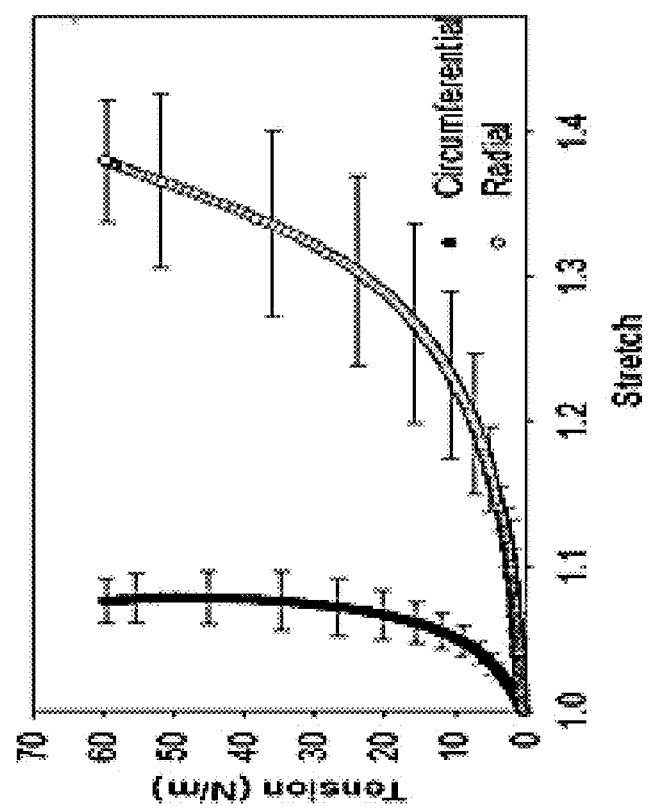
FIG. 1 graphically illustrates the stress-strain relationship of an untreated collagen scaffold after subdermal implantation in a control environment for four weeks.

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

The present invention is generally directed to medical devices (e.g., replacement heart valves, blood vessels, arteries, veins, etc.) that have been treated with phenolic compounds and a method of treating such medical devices with phenolic compounds so as to improve the characteristics of the devices when implanted in hyperglycemic environments that can cause glycoxidation and can result in inflammation, calcification, and stiffness associated with the medical devices, as is the case when implanted into diabetic patients. It is believed that glycated extracellular matrix proteins can alter cell function because of the interaction between the cells and AGEs. It is an object of the present disclosure to reduce the ability of AGEs to bind to such proteins by treatment of scaffolds with a phenolic compound. Problems associated with glycated extracellular matrix proteins can include the generation of an oxidative stress-dependent chronic inflammatory process, the induction of osteoblastic differentiation of pericytes; thus contributing to vascular calcification, alteration of the alignment of endothelial cells, thus contributing to atherosclerosis; the modification of basement membrane and endothelial progenitor cell interaction, thus contributing to impairment of angiogenesis and wound healing; and increase in the adhesion of neutrophils, thus contributing to the weakening of host-defense capacity in diabetic patients.

In general, any device can be treated with a phenolic compound as described by the methods herein to reduce the damaging effects of hyperglycemia upon implantation. The phenolic compound can function as a stabilizing agent and antioxidant to protect a treated device from glycoxidation, hence rendering the device "diabetes resistant."

Any medical device or scaffold can be treated with the phenolic compound. For instance, synthetic and natural biodegradable scaffolds can be treated with the phenolic compound, resulting in scaffolds that are resistant to glycoxidation upon implantation. Synthetic materials that can be used in implantable scaffolds, can include, but are not limited to polyesters such as polyglycolic acid, polylactic acid, and polycaprolactone; polytetrafluoroethylene, polyanhydride, polypropylene fumarate, polyvinyl alcohol, and polyethylene glycol. Natural/biologic materials that can be used in implantable scaffolds, can include, but are not limited to, decellularized extracellular matrix (ECM), collagen, elastin, fibrin, self-assembling peptide materials, polysaccharides such as alginate, and gelatin. These natural materials are available from, for example, porcine sources, although they can also be obtained from other sources, such as bovine or ovine. The synthetic or natural/biologic material can be formed into various scaffolds for implantation, by methods known to those of ordinary skill in the art. For example, the scaffolds can be used as replacement heart valves, arteries, other vessels, grafts or any other suitable, implantable medical device.

In one particular embodiment, the scaffold to be treated can be a decellularized collagen scaffold, which can be used as a replacement heart valve or heart valve leaflet. In another embodiment, the scaffold to be treated can be a decellularized elastin scaffold, which can be used as a replacement artery or other vessel. Whether the scaffold to be treated is collagen or elastin-based, numerous decellularization protocols can be followed, as are known in the art, to remove any cells and other cellular material from the donor tissue and provide an extracellular matrix for treatment with a phenolic compound.

One example of a decellularization protocol involves treating a collagen scaffold to be decellularized with detergents and enzymes. For instance, after the starting material (e.g., heart valve, vessel, etc. from a porcine, bovine, or any other suitable source) is harvested, excess tissue can be trimmed away and the material can be washed in distilled water. Next, the material can be placed in double-distilled water (ddH$_2$O) for a period of about 12 to 24 hours at 4° C. to induce hypotonic shock and cell lysis. The material can then be rinsed with ddH$_2$O. Next, the material can be treated with 0.05 Molar (M) sodium hydroxide (NaOH) for a period of about 2 hours at room temperature and under agitation. Next, the material can be rinsed with ddH$_2$O and placed in 70% ethanol (EtOH) for a period of about 20 minutes at room temperature. The material can then be rinsed with ddH$_2$O and incubated for a period of about 12-24 hours at room temperature in a decellularization solution. The decellularization solution can include 0.5% sodium dodecyl sulfate (SDS), 0.5% polyoxyethylene octyl phenyl ether (Triton X-100), 0.5% deoxycholate, and 0.2% ethylenediaminetetraacetic acid (EDTA) in 50 millimolar (mM) tris(hydroxymethyl) aminomethane, pH 7.5. After rinsing incubation in the decellularization solution, the material can be rinsed with ddH$_2$O multiple times, then rinsed in 70% EtOH to remove detergents, and incubated in ddH$_2$O at room temperature for a period of about 2 hours, after which the material can again be rinsed with ddH$_2$O. Next, the material can be incubated under agitation in a solution containing deoxyribonuclease (DNAse), ribonuclease (RNAse), and magnesium chloride (MgCl$_2$) at a temperature of 37° C. for a period of 36-48 hours. The concentration of DNAse and RNAse used can be around 360 mU/mL. The material can then be rinsed in ddH$_2$O, after which it can be sterilized by being placed in 70% EtOH at room temperature for a period of about 12-24 hours. After sterilization, aseptic/sterile technique can be used to remove any debris or extraneous tissue from the material. Then, the material can be washed with sterile ddH$_2$O and stored in sterile ddH$_2$O containing a 1% antibiotic/antimycotic by volume, such as Pen-Strep or any other suitable antibiotic and/or protease inhibitors.

Another example of a decellularization protocol involves treating an elastin scaffold to be decellularized with detergents and enzymes. For instance, after the starting material (e.g., carotid artery) is harvested and cleaned in 0.9% saline over ice, where extraneous tissue, fatty tissue and blood clots are removed from the artery. Then, each artery can be cut into segments that are about 5 centimeters long. Then, 3 segments can be placed in a 50 milliliter conical tube filled with a 0.1 M sodium hydroxide (NaOH) solution. The tubes can then be incubated for 24 hours at 37° C. in a shaking water bath. After the 24 hour NaOH treatment, the arteries can be transferred to a large beaker filled with ddH$_2$O and rinsed about 10 times under agitation for a period of about 5 minutes per rinse, or until the rinse water had a pH of about 8. The resulting elastin-based scaffolds can then be sterilized by being placed in 70% EtOH at room temperature for a period of about 12-24 hours. After sterilization, aseptic technique can be used to remove any debris or extraneous tissue from the material. Then, the material can be washed with sterile ddH$_2$O and stored in sterile phosphate buffered saline (PBS) or sterile ddH$_2$O containing 1% antibiotics, such as Pen-Strep or any other suitable antibiotic and/or protease inhibitors.

After decellularization, the resulting collagen or elastin-based scaffold (i.e., extracellular matrix) or other suitable implantable medical device can be treated with a phenolic compound, which can bind to the elastin and collagen and can act as an antioxidant, thus preventing the damaging effects of glycoxidation that occurs in diabetic patients. Natural or phenolic compounds can be used to treat the scaffolds or implants that to prevent glycoxidation of the implants that can be associated with a hyperglycemic environment.

Phenolic compounds encompassed by the present invention include any compound that includes at least one phenolic group bound to a hydrophobic core. While not wishing to be bound by any particular theory, it is believed that interaction between the phenolic compound and scaffold components such as collagen and elastin include aspects involving both the hydroxyl group as well as the hydrophobic core of the molecules. In particular, it is believed that phenolic compounds can stabilize the collagen and elastin proteins through both steric means and bond formation and thereby protect sites on the protein susceptible to glycoxidation. Specifically, it is believed that hydroxyl groups of a phenolic compound can bind collagen or elastin multivalently, for instance via hydrogen bond formation with amino acid residues such as polar amino acid residues including methionine, glycine and proline, such that multiple proteins can interact with a single molecule to create a three-dimensional cross-link structure involving multiple collagen or elastin molecules. Moreover, in certain embodiments, the phenolic compounds of the present invention can include one or more double bonds, with which the phenolic compounds can covalently bind to the collagen or elastin, forming an even stronger and more permanent protective association between the phenolic compound and the collagen or elastin of the extracellular matrix scaffold. Thus, the association between the phenolic compound and the protein molecules are believed to protect specific binding sites on the protein from reactive oxygen species associated with glycoxidation.

Phenolic compounds encompassed by the present invention include materials including a hydrophobic core and one or more phenol groups extending from the hydrophobic portion of the molecule. For instance, exemplary phenolic compounds of the invention can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

Phenolic compounds of the invention can include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like.

In one preferred embodiment, the phenolic compounds of the invention can be tannins and derivatives thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

Tannic acid is a common naturally derived tannin. Tannic acid, as a cross-linking agent, is similar in many properties to that of many fixatives often used in the preparation and formation of xenograft or allograft tissue implants, for instance glutaraldehyde fixatives. In one embodiment, the present invention is directed to utilization of the disclosed agents for stabilization of collagen or elastin scaffolds in vivo to prevent glycoxidation. Accordingly, in such embodiments, biocompatibility and cytotoxicity of the agents can be of importance in preparation of therapeutics including the disclosed compounds. At one time, tannic acid-containing preparations were suspected of causing hepatotoxicity. This toxicity has since been primarily attributed to poor purity of the preparations and the inclusion of toxic gallic acid residues in the compositions. Accordingly, in one embodiment, the present invention is directed to compositions including high purity tannic acid, with little or no free gallic acid residue included in the compositions. For example, in one embodiment, the compositions of the present invention can include less than about 5% free gallic acid residue in the preparation. In one embodiment, the compositions of the present invention can include between about 1% and about 5% free gallic acid residue in the composition.

In one preferred embodiment of the present invention, compositions are disclosed comprising an effective amount of pentagalloyl glucose (PGG), having the chemical structure set forth below:

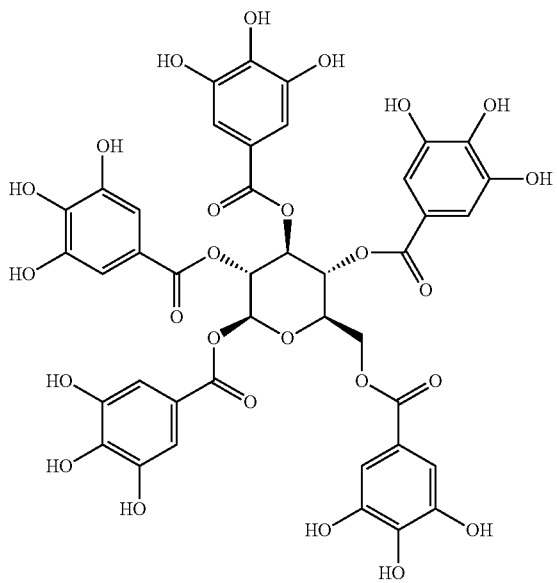 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

PGG includes the hydrophobic core of tannic acid as well as multiple phenolic hydroxy groups, but does not possess the outer gallic acid residues and the hydrolyzable ester bonds associated with tannic acid. Thus, the possibility of release of free gallic acid residues over the course of a long-term application process can be prevented in one embodiment of the invention through utilization of a compound having no gallic acid residues, such as PGG, as the selected agent.

In general, the phenolic compounds described herein can be applied to a collagen or elastin scaffold or any other material to be implanted into a diabetic environment by treating the scaffolds with a solution containing the phenolic compounds. For instance, treatment solutions disclosed herein can include one or more phenolic compounds in a concentration in a carrier, such as saline, that can vary over a wide range, with a preferred concentration generally depending on such factors as the particular application, the type of implant to be treated with the phenolic compound, and the location of the implant in the body. For example, in one embodiment, a composition of the invention can include one or more phenolic compounds at a concentration from about 0.0001% to about 10%. (Unless otherwise noted, all concentrations reported herein are weight/volume percentages.) In another embodiment of the present invention, the disclosed treatment solution can include concentrations of a phenolic compound ranging from about 0.001% to about 5.0%, such as from about 0.01% to about 3.0%. In still other embodiments, the concentration of the phenolic compound in the treatment solution can range from about 0.05% to about 2.0%, such as from about 0.1% to about 1.0%. It should be noted, however, that while these exemplary concentrations are effective in certain embodiments, the invention encompasses solutions comprising a wider range of phenolic compound concentrations. For example, actual concentrations used may be influenced by the location of the implanted scaffold, desired incubation time or temperature for scaffold treatment, and preferred pH.

Scaffolds of the present invention can be treated with a phenolic solution that includes additional agents, in addition to the phenolic compounds. Such agents can be active agents, providing direct benefit to the implanted scaffolds in addition to the stabilization provided by the phenolic compound, or may be supporting agents, improving delivery, compatibility, or reactivity of other agents in the composition. For example, in one embodiment, the scaffolds can also be treated with a gallic acid scavenger, for example ascorbic acid or glutathione, so as to prevent the release of free gallic acid residues.

A phenolic solution for treating scaffolds of the invention can include one or more buffers as are generally known in the art. For example, a solution including one or more phenolic compounds and having a pH from about 4.0 to about 9.0 may be formulated with inclusion of a biocompatible buffer such as distilled water, saline, phosphate buffers, borate buffers, HEPES, PIPES, and MOPSO. In one embodiment, a composition of the invention may be formulated to have a pH of between about 5.5 and about 7.4.

In one particular embodiment, the scaffolds to be implanted can be treated with a solution containing a phenolic compound as follows. For example, decellularized collagen or elastin scaffolds can be rinsed with sterile phosphate buffered saline (PBS). The scaffolds can then be immersed in a solution containing a sterile phenolic compound, such as pentagalloyl glucose (PGG) in a 4-(2-hydroxyethyl)-1-piperazineethanesulfonic acid (HEPES) solution in saline containing 20% isopropanol, or any other suitable concentration of isopropanol, where the solution has a pH between 4.0 and 9, such as a pH between 5.5 and 7.4, such as a pH of 5.5. The concentration of the PGG in the solution can range from about 0.01% to about 3.0%, such as from about 0.05% to about 2.0%, such as from about 0.1% to about 1.0%. The concentration of the HEPES solution in saline can be from about 10 millimolar (mM) to about 100 mM, such as from about 15 mM to about 80 mM, such as from about 25 mM to about 75 mM, such as about 50 mM.

Once placed in the PGG solution, the scaffolds can be incubated at room temperature under agitation and with protection from light for a period of from about 1 minute to about 168 hours, such as from about 2 hours to 96 hours, such as from about 4 hours to 48 hours depending on the concentration of the PGG in solution. For instance, the scaffolds can be incubated for a period of from about 12 hours to about 24 hours at room temperature, under agitation, and with protection from light. After this incubation step, the scaffolds can be washed in sterile PBS, then incubated in sterile PBS under agitation for a period of about 1 to 4 hours at room temperature. The scaffolds can thereafter be rinsed with sterile PBS. Next, the scaffolds can be stored at a temperature of from about 2° C. to about 8° C. in sterile water or PBS containing a protease inhibitor and antibiotics. The concentration of the protease inhibitor in the sterile water or PBS can range from about 0.01% to about 5%, such as from about 0.05% to about 2.5%, such as from about 0.1% to about 1%. The concentration of the antibiotic in the sterile water or PBS can likewise range from about 0.01% to about 5%, such as from about 0.05% to about 2.5%, such as from about 0.1% to about 1%. Examples of suitable protease inhibitors can include P8340 (Sigma), (epsilon)-Aminocaproic acid, Benzamidine-HCl, Bestatin-HCl, EDTA-Na$_2$, EGTA, Pepstatin A, PMSF, or combinations thereof. Examples of suitable antibiotics can include Pen-Strep, Amphotericin B, Gentamycin, Chloroamphenicol, Neomycin, or combinations thereof. Alternatively, the scaffolds can be stored at a temperature of from about 2° C. to about 8° C. in sterile water or PBS containing sodium azide. The concentration of the sodium azide in the water or PBS can range from about 0.005% to about 0.08%, such as from about 0.01% to about 0.06%, such as from about 0.02% to about 0.04%.

The scaffolds/devices and methods as disclosed herein may be better understood with reference to the following examples.

Example 1

Example 1 refers to FIGS. 1-10 and describes the decellularization process, the PGG treatment process, and implantation into an in vivo model, where untreated collagen and elastin scaffolds were subdermally implanted in a control/non-diabetic in vitro environment and a diabetic in vitro environment to determine how a diabetic environment affects the denaturation temperature of the decellularized collagen and elastin scaffolds. Then, collagen scaffolds treated with PGG and untreated scaffolds were placed in an in vivo diabetic environment to determine how treatment with PGG affects the mechanical properties and the denaturation temperature of a collagen scaffold in a diabetic environment.

First, the collagen scaffolds were prepared via a decellularization protocol similar to that discussed above. The collagen scaffolds were sourced from porcine heart valves that were harvested, cleaned of excess tissue over ice, and washed in distilled water. Valves were placed in double-distilled water (ddH$_2$O) overnight (12-24 hours) at 4° C. to induce hypotonic shock and cell lysis. After rinsing, the valves were treated with 0.05 M sodium hydroxide (NaOH) for 2 hours at room temperature under agitation. Valves were rinsed with ddH$_2$O and placed in 70% ethanol (EtOH) for 20 minutes at room temperature. After rinsing with ddH$_2$O, cells were incubated overnight (12-24 hours) at room temperature in decellularization solution comprised of 0.5% sodium dodecyl sulfate (SDS), 0.5% Triton X-100, 0.5% deoxycholate, and 0.2% ethylenediaminetetra-acetic acid (EDTA) in 50 mM tris(hydroxymethyl)aminomethane, pH 7.5. After rinsing with ddH$_2$O and 70% EtOH 5 times, the valves were incubated in a solution containing 360 mU/mL of each of deoxyribonuclease (DNAse) and ribonuclease (RNAse) for 48 hours at 37° C. under agitation. After rinsing with ddH$_2$O, valves were sterilized in 70% EtOH overnight (12-24 hours) at room temperature. Under sterile conditions, the aortic cusps were dissected away from the aortic wall. The cusps were washed with sterile ddH$_2$O and stored in sterile ddH$_2$O with 1% antibiotic/antimycotic (Pen-Strep) at 4° C. Each individual decellularized cusp served as a collagen scaffold.

Meanwhile, the elastin scaffolds were prepared following an alkaline extraction protocol as discussed above with minor modifications. Generally, fresh porcine carotid arteries (60-80 mm long, 5-6 mm in diameter) were decellularized by incubation in 0.1 M NaOH solution at 37° C. for 24 hours followed by rinsing with deionized water until the pH was neutral. The scaffolds were then rinsed and stored in sterile PBS.

Next, a portion of the collagen and elastin scaffolds were treated with pentagalloyl glucose (PGG) to compare its effect on the collagen and elastin scaffolds in diabetic environments. For the PGG treatment, the collagen and elastin scaffolds were rinsed with sterile PBS. Scaffolds were then treated a solution containing sterile 0.1% PGG in 50 mM 4-(2-hydroxyethyl)-1-piperazineethanesulfonic acid (HEPES) solution in saline (pH 5.5) containing 20% isopropanol overnight (12-24 hours) at room temperature under agitation and protected from light. After treatment, the PGG-treated scaffolds were washed in sterile PBS and were stored in sterile PBS containing 1% protease inhibitor (Sigma P8340) and 1% Pen-Strep at 4° C.

Next, the collagen and elastin scaffolds were implanted into an in vivo model (control untreated, control PGG-treated, diabetic untreated, and diabetic PGG-treated for both collagen and elastin scaffolds, with a sample size of 20 for each condition). Adult male Sprague-Dawley rats having a weight of 300-350 grams were used to model normal and diabetic conditions. Half of the rats were rendered diabetic via a single dose of 55 milligrams/kilogram (mg/kg) streptozotocin (STZ) in 0.1 molar (M) citrate buffer having a pH of 5 by tail vein injection. The other half of the rats were control rates and were administered the same volume of citrate buffer only. Diabetes was established within 3 days of STZ administration, as confirmed by a glucose concentration of greater than 400 milligrams/deciliter (mg/d L) in blood samples taken from the rats. From 2 to 4 units of isophane insulin was administered to the diabetic rats every other day (3-4 times per week) to maintain blood glucose in a range of from about 400 to about 600 mg glucose/dL blood. Blood glucose was monitored on the on the same day as insulin administration in the diabetic rats by using AlphaTRAK Blood Glucose Monitoring System (Abbott Laboratories, Abbott Park, Ill. Blood glucose level was determined every 5 days in the control rats.

Four weeks after STZ administration, rats were anesthetized using 1-2% isoflurane. The diabetic model rats were given 1 U of insulin pre-operatively. For implanting the collagen scaffolds, a small incision was made on the back of the rats, and two subdermal pouches were created by blunt dissection for two collagen scaffolds to be implanted per rat. The incision was closed with surgical staples, and the rats were given time to recover and given free access to food and water. Before implanting the elastin scaffolds, the acellular arteries serving as the elastin scaffolds were cut open longitudinally and into 1 centimeter (cm) by 3 cm samples, which were implanted subdermally as described for the collagen scaffolds (2 per rat). The blood glucose levels of the diabetic rats was monitored 3-4 times per week, and insulin was administered as needed to keep the blood glucose level in the desired range (400-600 mg glucose/dL of blood). After 4 weeks, the scaffolds were then explanted and stored according to their respective assay application. Throughout the implantation process through explantation, animals were provided with food and water ad libitum and were cared for by an attending veterinarian following National Institutes of Health guidelines for the care and use of laboratory animals (NIH publication #86-23 Rev. 1996).

Scaffolds for later histological analysis was placed in Karnovksy's Fixative (2.5% glutaraldehyde, 2% formalin, 0.1 M cacodylic acid, pH 7.4) and paraffin embedded. Scaffolds for mechanical analysis were stored in sterile PBS with 0.02% sodium azide ($NaN_3$) at 4° C. Tissues for later protein, calcium, and AGE analysis were flash frozen with liquid nitrogen and kept on dry ice until transferred to −20° C. for storage.

Mechanical Testing

For the mechanical testing of the collagen scaffolds, a 12 mm by 12 mm square was cut from a central region of the valve cusp, with one edge aligned along the circumferential direction and another edge aligned along the radial direction (n=5). Similarly, a 12 mm by 12 mm square specimen was cut from the elastin scaffolds, maintaining orientation of the circumferential and longitudinal axes of the artery/elastin scaffold. The biaxial testing method is as described in the article by J. Liao, E. M. Joyce, and M. S. Sacks entitled *Effects of decellularization on the mechanical and structural properties of the porcine aortic valve leaflet* (Biomaterials 2008; 29(0): 1065-74). Four markers were placed in the center or each specimen to track tissue deformation. Then, eight loops of 000 polyester suture of equal length were attached to the sample via stainless steel hooks, with two loops on each side of the square specimen. Specimens were pre-conditioned for 10 contiguous cycles, then loaded up to 60:60 N/m equibiaxial tension for the collagen scaffolds and 20:20 N/m tension for the elastin scaffolds. Tissue extensibility was characterized by $\lambda_{circ}$ and $\lambda_{rad}$, the maximum stretch ratio along the circumferential and radial directions, respectively. The biaxial testing was implemented with the samples completely immersed in pH 7.4 PBS at 37° C.

Differential Scanning Calorimetry (DSC)

To determine the thermal denaturation temperature ($T_d$), also known as shrinkage temperature, which is a well-known indicator of collagen crosslinking, samples (n=3) were subjected to differential scanning calorimeter (DSC Model 131, Setaram Instrumentation, Caluire, France) at a heating rate of 10° C./minute from 20° C. to 110° C. in a $N_2$ gas environment. $T_d$ was defined as the temperature at the endothermic peak.

The mechanical testing and DSC testing results are shown in FIGS. 1-5 for the collagen scaffolds and FIGS. 6-10 for the elastin scaffolds.

Figure 2:
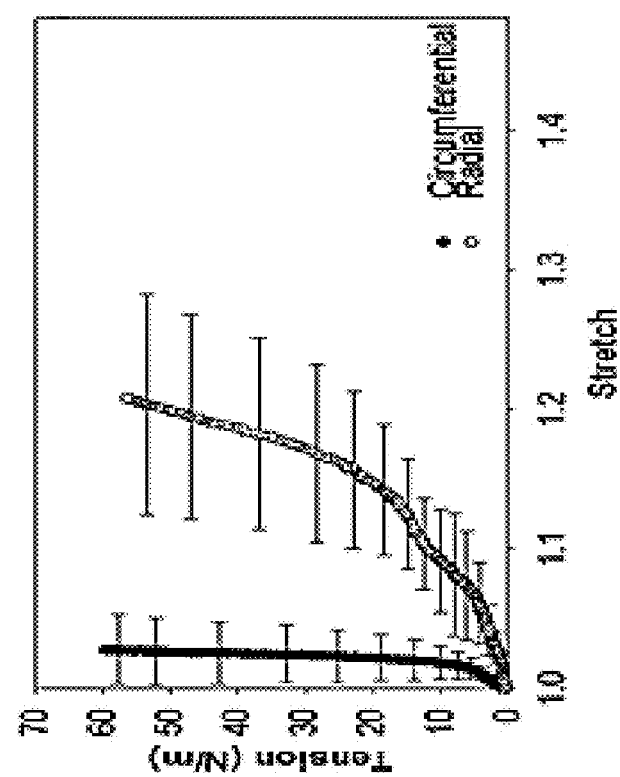
FIG. 2 graphically illustrates the stress-strain relationship of an untreated collagen scaffold after subdermal implantation in a diabetic environment for four weeks.

As shown through a comparison of in FIGS. 1-2, the untreated collagen scaffolds implanted in a diabetic environment (FIG. 2) exhibited a markedly increased stiffness in both the circumferential and radial directions compared to the untreated collagen scaffolds implanted in a control (non-diabetic) environment (FIG. 1). In other words, the collagen scaffolds in the diabetic environment had a lower stretch value in the circumferential direction and the radial direction as compared to the collagen scaffolds in the control/non-diabetic environment, indicating that the collagen scaffolds in the diabetic environment were stiffer than the collagen scaffolds in the control/non-diabetic environment. For instance, at a tension of 40 N/m in the circumferential direction, the untreated collagen scaffolds implanted in the control environment had a stretch value of about 1.05, while the untreated collagen scaffolds implanted in the diabetic environment had a stretch value of only about 1.0. Meanwhile, at a tension of 40 N/m in the radial direction, the untreated collagen scaffolds implanted in the control environment had a stretch value of about 1.3, while the untreated collagen scaffolds placed in the diabetic environment had a stretch value of only about 1.15. Thus, a comparison of FIGS. 1 and 2 shows that a diabetic environment increases the stiffness (reduces the stretch) of the collagen scaffolds.

Figure 3:
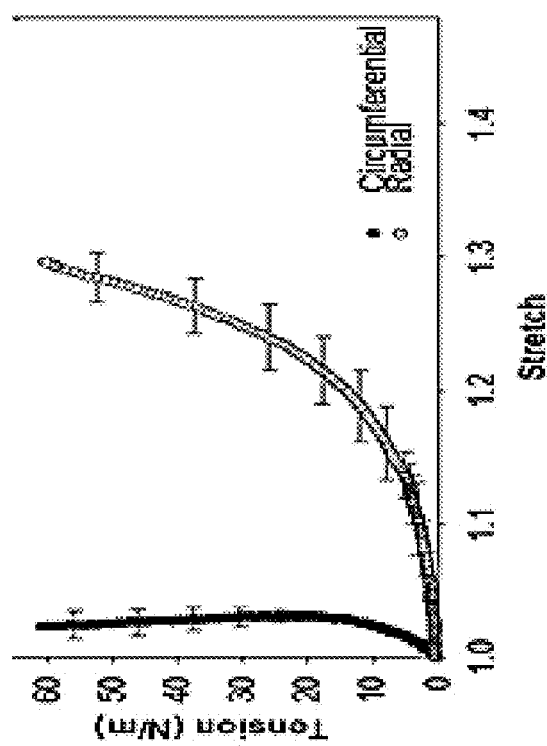
FIG. 3 graphically illustrates the stress-strain relationship of a pentagalloyl glucose (PGG)-treated collagen scaffold after subdermal implantation in a control environment for four weeks.
Figure 4:
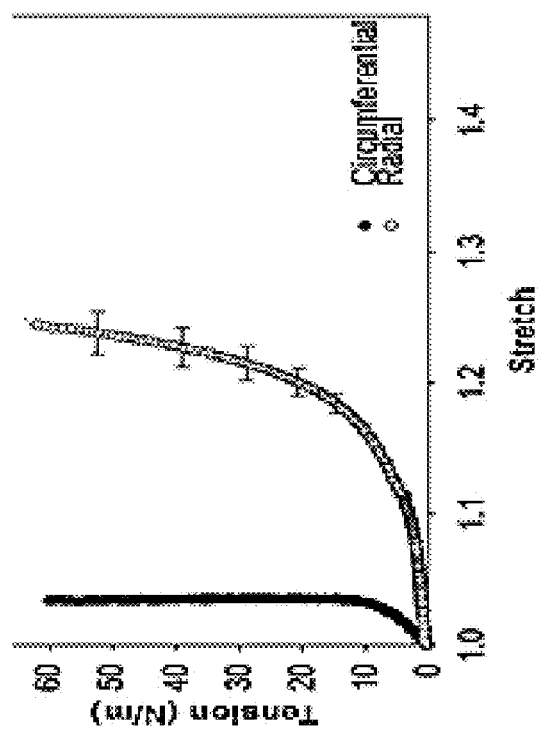
FIG. 4 graphically illustrates the stress-strain relationship of a PGG-treated collagen scaffold after subdermal implantation in a diabetic environment for four weeks.

Meanwhile, as shown through a comparison of FIGS. 3-4, the PGG-treated collagen scaffolds implanted in a diabetic environment (FIG. 4) exhibited a less-marked or no increase in stiffness in either the circumferential or radial directions compared to the PGG-treated collagen scaffolds implanted in a control (non-diabetic) environment (FIG. 3). In other words, treating the collagen scaffolds implanted in the diabetic environment with PGG (FIG. 4) prevented the increase in stiffness seen when implanting untreated collagen scaffolds in a diabetic environment (FIG. 2) versus a control environment (FIG. 1) so that the scaffolds exhibited properties similar to PGG-treated collagen scaffolds implanted in a non-diabetic environment. For instance, at a tension of 40 N/m in the circumferential direction, the PGG-treated collagen scaffolds implanted in the control environment had a stretch value of about 1.01, while the PGG-treated collagen scaffolds placed in a diabetic environment also had a stretch value of about 1.01. Meanwhile, at a tension of 40 N/m in the radial direction, the PGG-treated collagen scaffolds implanted in the control environment had a stretch value of about 1.2, while the PGG-treated collagen scaffolds placed in the diabetic environment had a stretch value of about 1.25. Thus, a comparison of FIGS. 2-4 shows that treating a collagen-scaffold with PGG before implanting the scaffold in a diabetic environment prevents the increase in stiffness of the collagen scaffold seen compared to when an untreated collagen scaffold is implanted in a diabetic environment so that the stretch value of the PGG-treated collagen scaffold in a diabetic environment is approximately the same as the stretch value of a PGG-treated collagen scaffold in a non-diabetic environment. Remarkably, the PGG-treatment appeared to halt the stiffening effect observed in collagen scaffolds implanted in the diabetic rats, as there was no statistical difference in the mechanical properties in the PGG-treated collagen scaffolds placed in the diabetic environment compared to the control environment.

Figure 5:
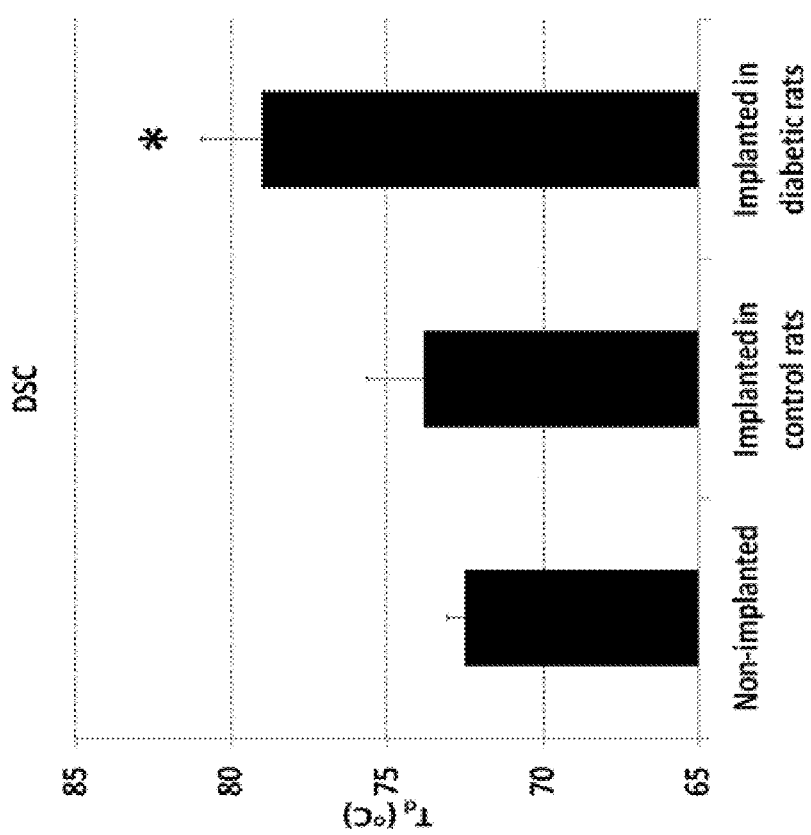
FIG. 5 shows the thermal denaturation temperatures ($T_d$) of non-implanted collagen scaffolds compared to collagen scaffolds that were subdermally implanted in control rats and diabetic rats.

Next, DSC was used to determine the thermal denaturation temperature of non-implanted collagen scaffolds with those implanted either into a control environment or a diabetic environment. As shown in FIG. 5, the collagen scaffolds implanted in a diabetic environment had a thermal denaturation temperature of about 79° C., while the collagen scaffolds implanted in a control environment had a thermal denaturation temperature of about 74° C. This increase suggests that diabetes induced stiffening and crosslink formation is a concern in collagen scaffolds.

Figure 6:
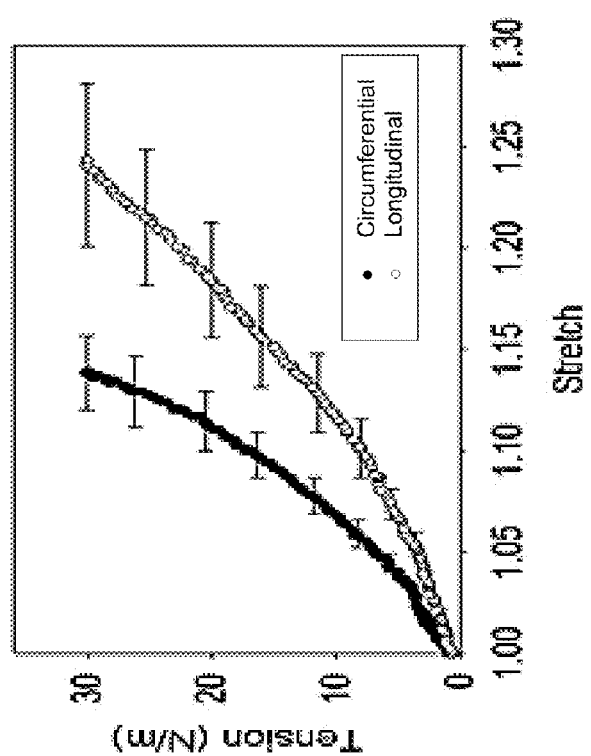
FIG. 6 graphically illustrates the stress-strain relationship of an untreated elastin scaffold after subdermal implantation in a control environment for four weeks.
Figure 7:
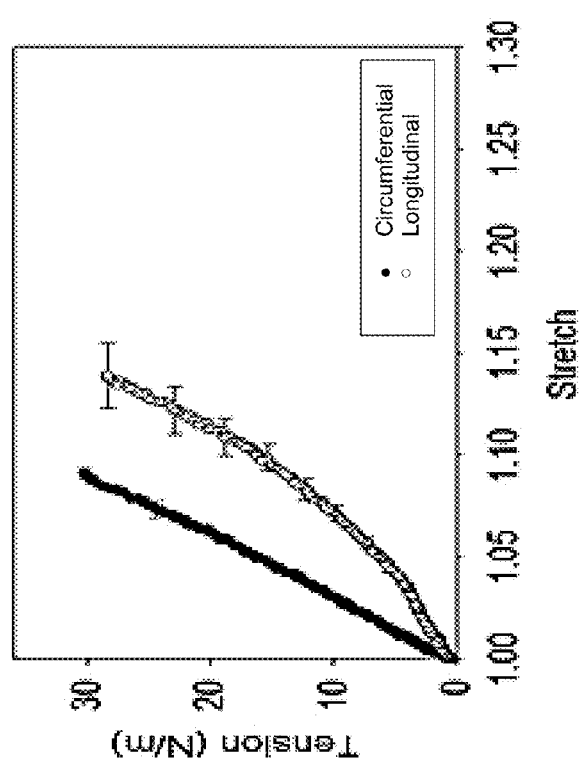
FIG. 7 graphically illustrates the stress-strain relationship of an untreated elastin scaffold after subdermal implantation in a diabetic environment for four weeks.

Next, as shown through a comparison of in FIGS. 6-7, the untreated elastin scaffolds implanted in a diabetic environment (FIG. 7) exhibited a markedly increased stiffness in both the circumferential and longitudinal direction compared to the untreated elastin scaffolds implanted in a control (non-diabetic) environment (FIG. 6). In other words, the elastin scaffolds in the diabetic environment had a lower stretch value in the circumferential direction and the longitudinal direction as compared to the elastin scaffolds in the control/non-diabetic environment, indicating that the elastin scaffolds in the diabetic environment were stiffer than the elastin scaffolds in the control/non-diabetic environment. For instance, at a tension of 20 N/m in the circumferential direction, the untreated elastin scaffolds implanted in the control environment had a stretch value of about 1.1, while the untreated elastin scaffolds implanted in the diabetic environment had a stretch value of only about 1.0. Meanwhile, at a tension of 20 N/m in the longitudinal direction, the untreated elastin scaffolds implanted in the control environment had a stretch value of about 1.17, while the untreated elastin scaffolds placed in the diabetic environment had a stretch value of only about 1.1. Thus, a comparison of FIGS. 6 and 7 shows that a diabetic environment increases the stiffness (reduces the stretch) of the elastin scaffolds.

Figure 8:
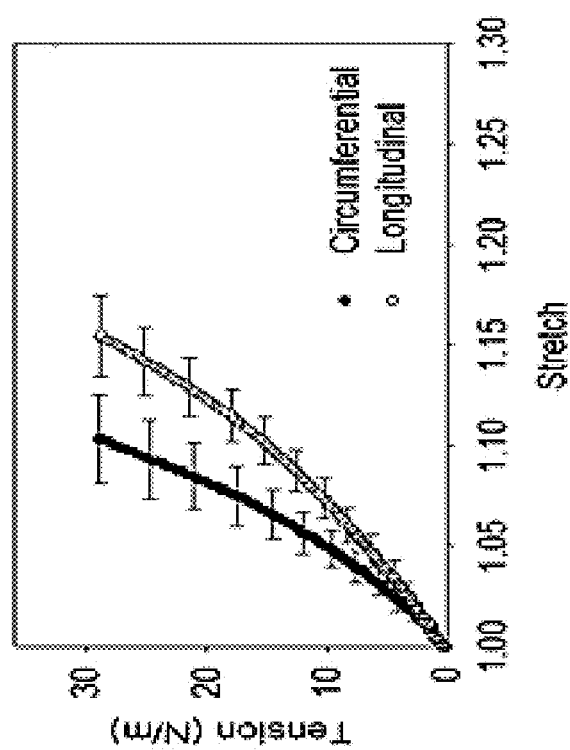
FIG. 8 graphically illustrates the stress-strain relationship of a PGG-treated elastin scaffold after subdermal implantation in a control environment for four weeks.
Figure 9:
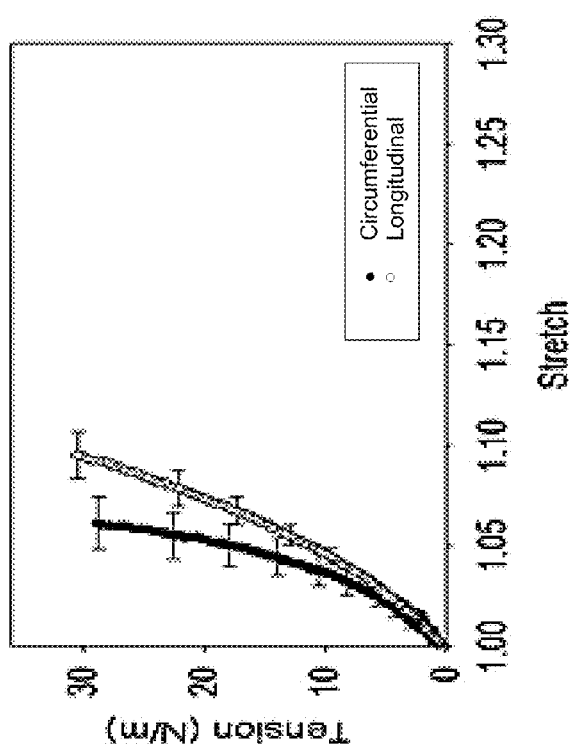
FIG. 9 graphically illustrates the stress-strain relationship of a PGG-treated elastin scaffold after subdermal implantation in a diabetic environment for four weeks.

Meanwhile, as shown through a comparison of FIGS. 8-9, the PGG-treated elastin scaffolds implanted in a diabetic environment (FIG. 9) exhibited a less-marked or no increase in stiffness in both the circumferential and longitudinal directions compared to the PGG-treated elastin scaffolds implanted in a control (non-diabetic) environment (FIG. 8). In other words, treating the elastin scaffolds implanted in the diabetic environment with PGG (FIG. 9) prevented the increase in stiffness seen when implanting untreated elastin scaffolds in a diabetic environment (FIG. 7) versus a control environment (FIG. 6) so that the elastin scaffolds exhibited properties similar to PGG-treated elastin scaffolds implanted in a non-diabetic environment. For instance, at a tension of 20 N/m in the circumferential direction, the PGG-treated elastin scaffolds implanted in the control environment had a stretch value of about 1.05, while the PGG-treated elastin scaffolds placed in a diabetic environment also had a stretch value of about 1.05. Meanwhile, at a tension of 20 N/m in the longitudinal direction, the PGG-treated elastin scaffolds implanted in the control environment had a stretch value of about 1.12, while the PGG-treated elastin scaffolds placed in the diabetic environment had a stretch value of about 1.09. Thus, a comparison of FIGS. 7-9 shows that treating a elastin-scaffold with PGG before implanting the scaffold in a diabetic environment prevents the increase in stiffness of the elastin scaffold seen compared to when an untreated elastin scaffold is implanted in a diabetic environment so that the stretch value of the PGG-treated elastin scaffold in a diabetic environment is approximately the same as the stretch value of a PGG-treated elastin scaffold in a non-diabetic environment. Remarkably, the PGG-treatment appeared to halt the stiffening effect observed in elastin scaffolds implanted in the diabetic rats, as there was no statistical difference in the mechanical properties in the PGG-treated elastin scaffolds placed in the diabetic environment compared to the control environment.

Figure 10:
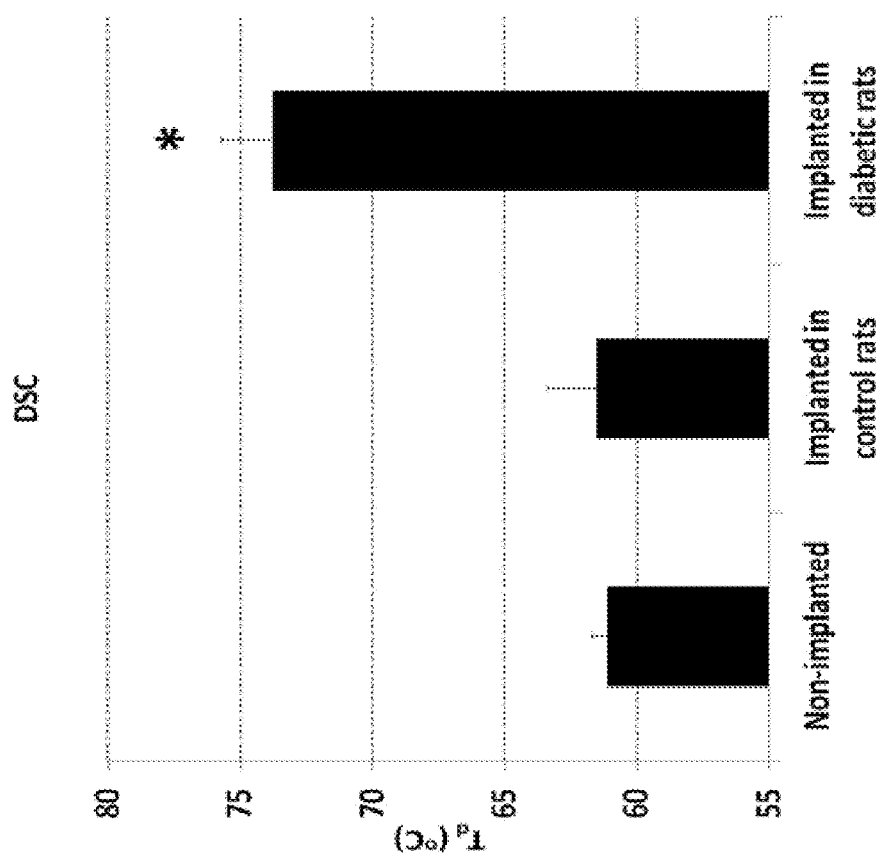
FIG. 10 shows the thermal denaturation temperatures ($T_d$) of non-implanted elastin scaffolds compared to collagen scaffolds that were subdermally implanted in control rats and diabetic rats.

Next, DSC was used to determine the thermal denaturation temperature of non-implanted elastin scaffolds with those implanted either into a control environment or a diabetic environment. As shown in FIG. 10, the elastin scaffolds implanted in a diabetic environment had a thermal denaturation temperature of about 74° C., while the collagen scaffolds implanted in a control environment had a thermal denaturation temperature of about 62° C. This increase suggests that diabetes induced stiffening and crosslink formation is a concern in elastin scaffolds.

Example 2

Figure 11:
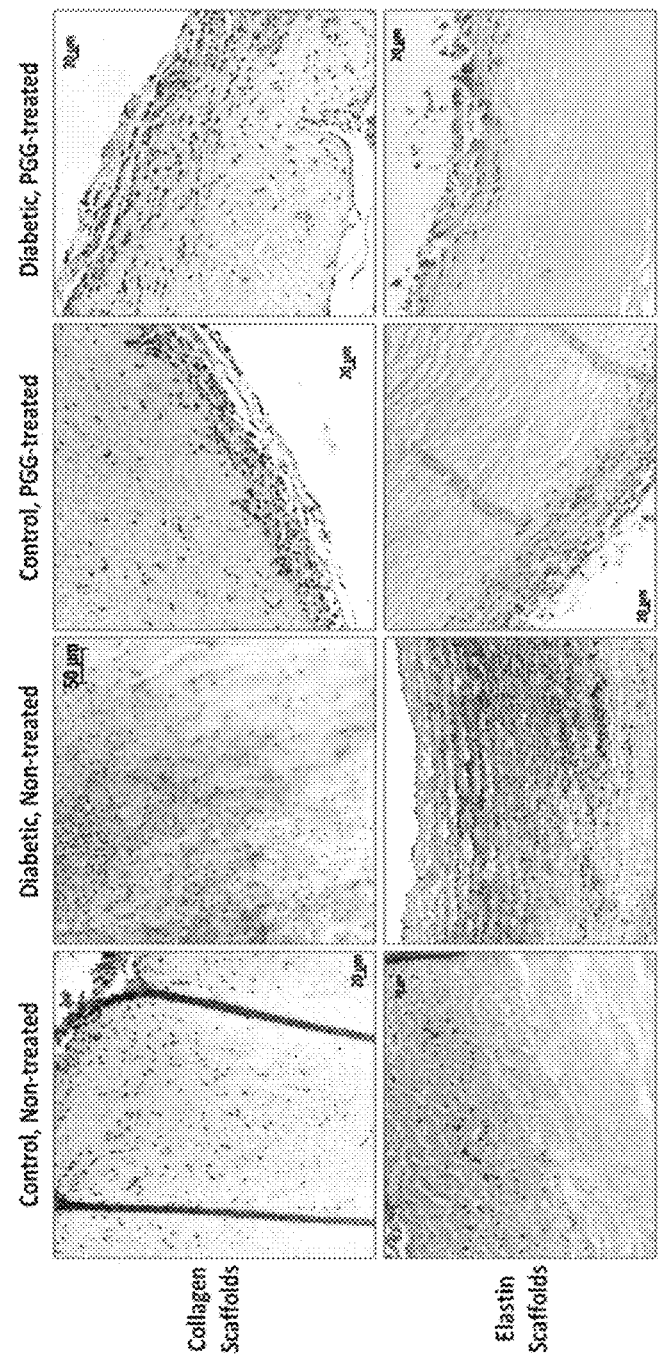
FIG. 11 illustrates the general absence of carboxymethyl lysine (CML), an AGE, in (1) control, non-treated collagen and elastin scaffolds, (2) control, PGG-treated collagen and elastin scaffolds, and (3) diabetic, PGG-treated collagen and elastin scaffolds and the general presence of CML in diabetic, non-treated collagen and elastin scaffolds via immunohistochemical staining.

In Example 2, the untreated and PGG-treated collagen and elastin scaffolds of Example 1, either implanted in either a control or diabetic environment of Example 1, were explanted from the control or diabetic environment and analyzed to determine the presence of advanced glycation end products (AGE) N-epsilon-(carboxymethyl)lysine (CML). The results are shown in FIG. 11.

First, the presence of CML in the explanted untreated collagen or elastin scaffolds of Example 1 was detected using an immunohistochemistry assay. Untreated paraffin-embedded collagen scaffold samples were deparaffinized and rehydrated with water. The scaffold sections were then treated with 0.1% proteinase K in 10 mM Tris buffer, pH 7.5, at room temperature for 30 seconds to unmask the antigen sites. Endogenous peroxidases were blocked with 0.3% hydrogen peroxide ($H_2O_2$) in 0.3% horse normal serum. Sections were then permeabilized in 0.025% Triton X-100 in TBS for 10 minutes and then incubated in horse normal blocking serum for 20 minutes. Primary antibody (4 µg/mL mouse anti-CML) was applied for 1 hour at room temperature (incubation in TBS used as a negative control). A secondary biotinylated antibody (normal horse serum, biotinylated anti-mouse IgG rat adsorbed in TBS) was applied for 30 minutes at room temperature. ABC complex from Vectastain ABC it (Vector Laboratories, Burlingame, Calif.) was applied to sections for 30 minutes at room temperature. Sections were then developed with diaminobenzidine tetrahydrochloride (DAB) from a peroxidase substrate kit (Vector Laboratories) for 30 seconds under close microscopic watch. Reaction was halted in tap water, and the sections were counterstained in diluted hematoxylin (50% hematoxylin, 50% water) for 30 seconds.

After rinsing in water, sections were dehydrated, cleared, and mounted with Permount mounting medium (Fischer Scientific, Hampton, N.H.).

Immunohistochemical analysis for the PGG-treated-fixed tissue samples was performed in the same manner with the exception of the antigen-unmasking step. Instead of using proteinase K, sections were subjected to 10 mM citric acid monohydrate (pH 6.0) at a temperature between 90° C. and 100° C. for 25 minutes. Once the sections were cooled to room temperature, the same protocol as the untreated scaffold sections could be performed for the PGG-treated scaffold sections. Development in DAB also took longer, approximately 2 minutes. After treatment, the presence of CML was indicated by a brown or dark color on the tissue sections.

FIG. 11 illustrates the amount of CML staining in (1) an untreated collagen scaffold that was implanted in a control environment, (2) an untreated collagen scaffold that was implanted in a diabetic environment, (3) a PGG-treated collagen scaffold that was implanted in a control environment, (4) a PGG-treated collagen scaffold that was implanted in a diabetic environment, (5) an untreated elastin scaffold that was implanted in a control environment, (6) an untreated elastin scaffold that was implanted in a diabetic environment, (7) a PGG-treated elastin scaffold that was implanted in a control environment, and (8) a PGG-treated elastin scaffold that was implanted in a diabetic environment.

As shown in FIG. 11, the dark brown pigmentation on the non-treated collagen and non-treated elastin scaffolds that were implanted in a diabetic environment indicates the presence of CML, a harmful AGE. Meanwhile, the dark brown pigmentation is absent from the PGG-treated collagen and PGG-treated elastin scaffolds that were implanted in a diabetic environment, indicating the absence of CML in the PGG-treated scaffolds. Thus, the PGG treatment effectively prevented the formation of CML on the scaffold, indicating that PGG can protect the scaffolds from the glycoxidation that is prevalent in diabetic environments.

Example 3

Next, in Example 3, the untreated and PGG-treated collagen and elastin scaffolds of Example 1 were explanted from the diabetic environment and analyzed for pentosidine, another biomarker for advanced glycation end products (AGEs).

Presence of pentosidine was detected using standard fluorescence detection. Explanted untreated and PGG-treated collagen and elastin scaffolds were digested in a solution of collagenase in HEPES buffer (50 mM HEPES, 10 mM calcium chloride ($CaCl_2$), collagenase type I Sigma—100 U/sample). Digestion occurred a pH of 7.5 at 37° C. until all tissue samples were fully digested. Collagenase solution with no tissue was used as a control. Upon digestion, tissues were centrifuged for 10 minutes at 12000 rpm at 22° C. The supernatant was collected and transferred to a new microfuge tube. 10×, 50×, and 100× dilutions of each supernatant were prepared. 250 microliters (μL) of each sample, including dilutions, were transferred into a black plate and read at 335 nm excitation, 385 nm emission. The final concentration of pentosidine was calculated and expressed as fluorescence units per milligram original tissue wet weight, as shown in FIG. 12.

Figure 12:
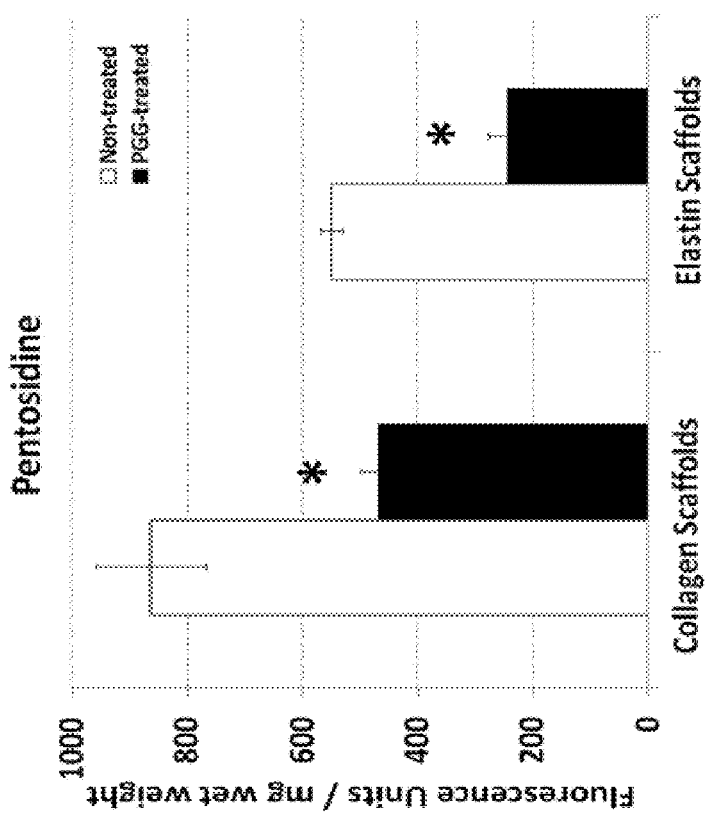
FIG. 12 compares the levels of pentosidine, an AGE, in non-treated and PGG-treated collagen and elastin scaffolds after subdermal implantation in a diabetic environment.

As shown in the chart of FIG. 12, an increased amount of fluorescence units/milligram of pentosidine was present in the untreated collagen and elastin scaffolds as compared to the PGG-treated collagen and elastin scaffolds. For instance, untreated collagen scaffolds contained about 875 fluorescence units/mg of pentosidine, while PGG-treated collagen scaffolds only contained about 450 fluorescence units/mg of pentosidine. Meanwhile, untreated elastin scaffolds contained about 575 fluorescence units/mg of pentosidine, while PGG-treated elastin scaffolds only contained about 225 fluorescence units/mg of pentosidine. This indicates that the PGG treatment effectively decreases the amount of AGE products binding to collagen and elastin scaffolds because the PGG-treated scaffolds contained lower levels of pentosidine.

Example 4

In Example 4, the untreated and PGG-treated collagen and elastin scaffolds of Example 1 were explanted from the diabetic environment and analyzed for malondialdehyde, a marker for oxidative stress and a by-product of lipid peroxidation.

Presence of MDA was detected using standard fluorescence detection. Explanted untreated and PGG-treated collagen and elastin scaffolds were digested in a solution of collagenase in HEPES buffer (50 mM HEPES, 10 mM calcium chloride ($CaCl_2$), collagenase type I Sigma—100 U/sample). Digestion occurred a pH of 7.5 at 37° C. until all tissue samples were fully digested. Collagenase solution with no tissue was used as a control. Upon digestion, tissues were centrifuged for 10 minutes at 12000 rpm at 22° C. The supernatant was collected and transferred to a new microfuge tube. 10×, 50×, and 100× dilutions of each supernatant were prepared. 250 microliters (μL) of each sample, including dilutions, were transferred into a black plate and read at 390 nm excitation, 460 nm emission. The final concentration of MDA was calculated and expressed as fluorescence units per milligram original tissue wet weight, as shown in FIG. 13.

Figure 13:
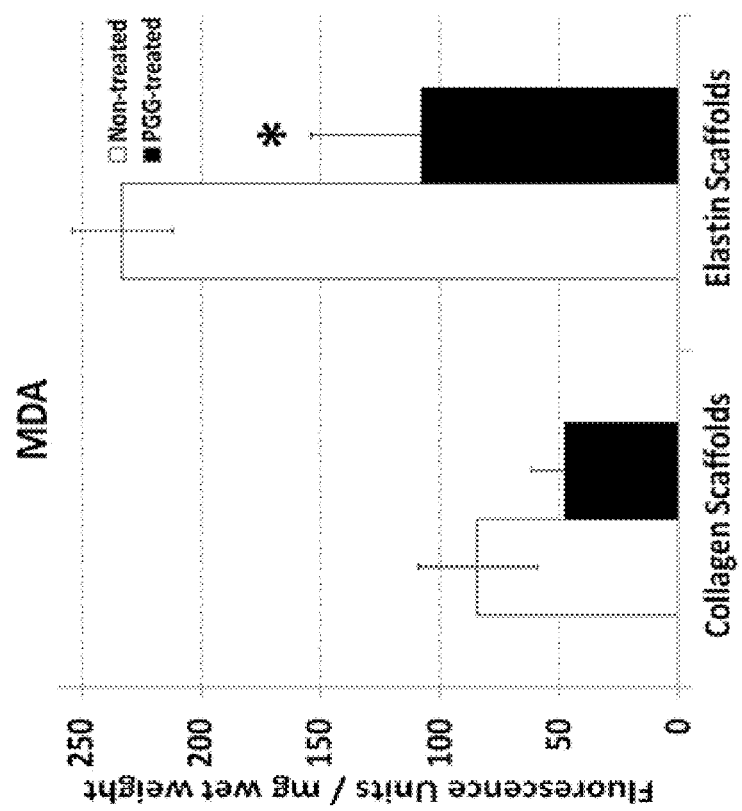
FIG. 13 compares the levels of malondialdehyde (MDA), a lipid peroxidation product, in non-treated and PGG-treated collagen and elastin scaffolds after subdermal implantation in a diabetic environment.

As shown in the chart of FIG. 13, an increased amount of fluorescence units/milligram of MDA was present in the untreated collagen and elastin scaffolds as compared to the PGG-treated collagen and elastin scaffolds. For instance, untreated collagen scaffolds contained about 80 fluorescence units/mg of MDA, while PGG-treated collagen scaffolds only contained about 50 fluorescence units/mg of MDA. Meanwhile, untreated elastin scaffolds contained about 225 fluorescence units/mg of MDA, while PGG-treated elastin scaffolds only contained about 100 fluorescence units/mg of MDA. This indicates that the PGG treatment effectively decreases the amount of lipid peroxidation products present because the PGG-treated scaffolds contained lower levels of MDA.

Example 5

In Example 5, the collagen and elastin scaffolds of Example 1 were analyzed by Hematoxylin and Eosin (H&E) staining as well as immunohistochemistry staining (vimentin, CD8, and CD68) to determine whether treatment with PGG affects inflammatory cell infiltration. The immunohistochemical staining was performed using the same protocol described above in Example 2 for the CML staining.

Figure 14:
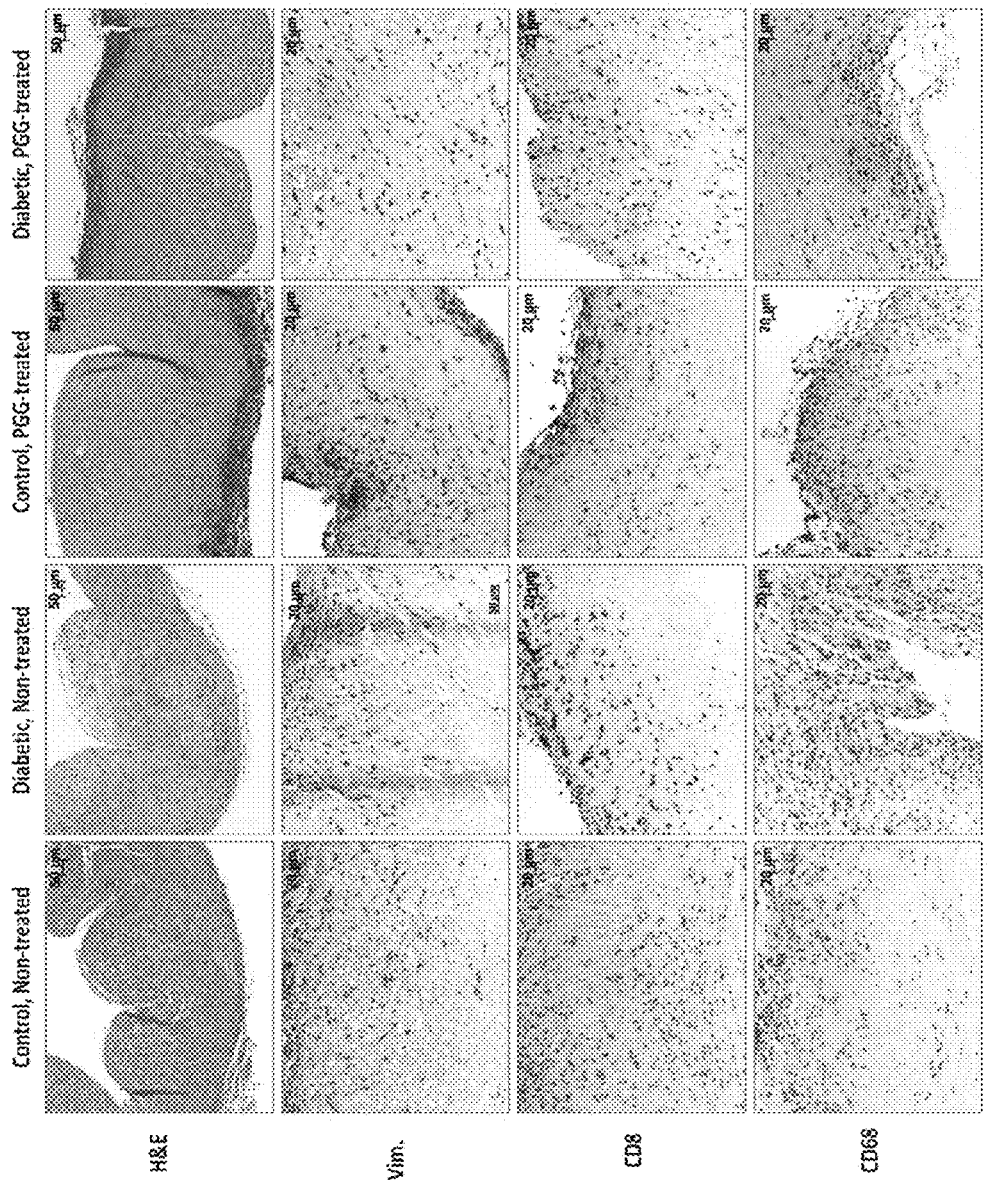
FIG. 14 illustrates the results of hematoxylin and eosin staining and immunohistochemistry staining of non-treated and PGG-treated collagen scaffolds after subdermal implantation in control and diabetic environments.
Figure 15:
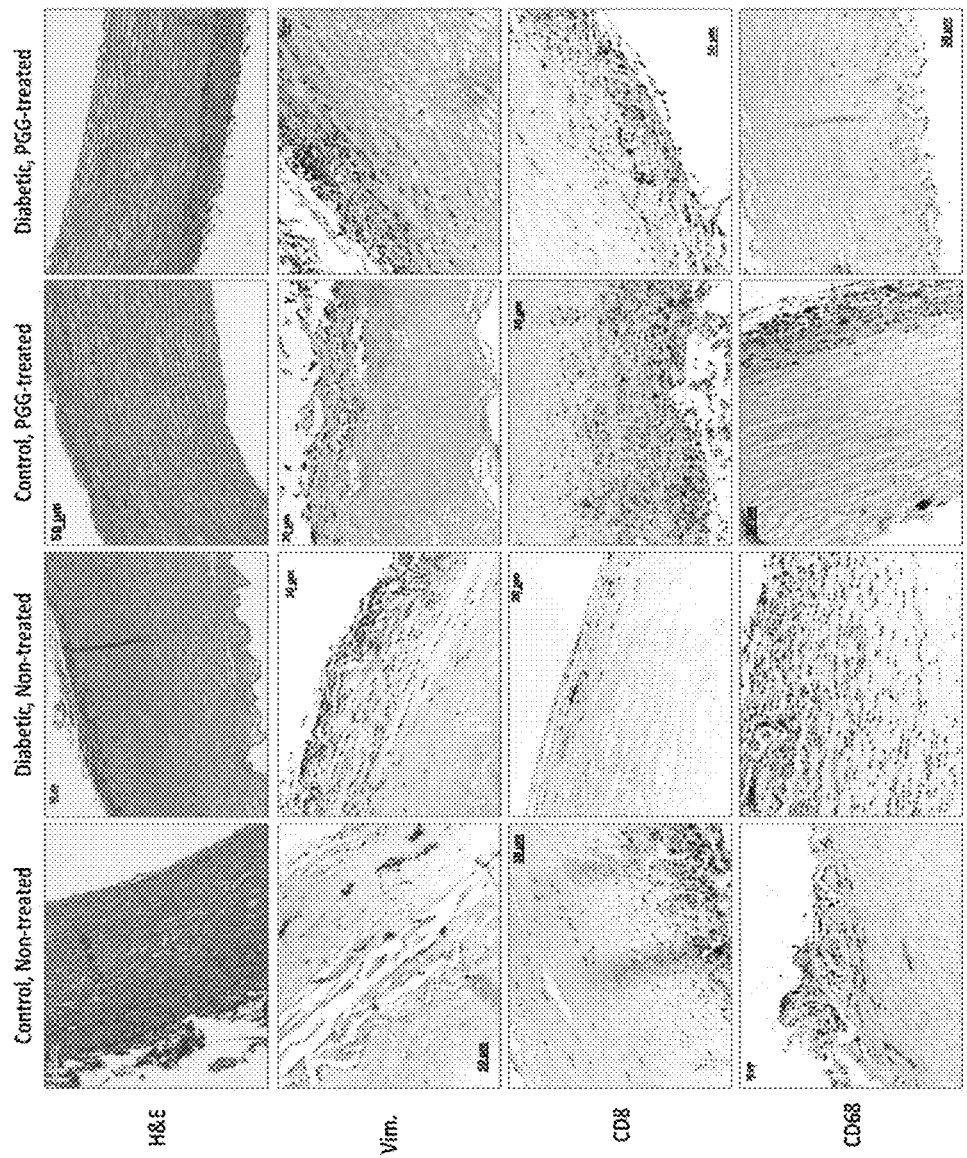
FIG. 15 illustrates the results of hematoxylin and eosin staining and immunohistochemistry staining of non-treated and PGG-treated elastin scaffolds after subdermal implantation in control and diabetic environments.

The staining results for the collagen scaffolds are shown in FIG. 14 and the staining results for the elastin scaffolds are shown in FIG. 15. As shown in FIGS. 14 and 15, H&E staining demonstrated host cell infiltration into all of the scaffolds, as indicated by the presence of dark purple nuclei. The infiltration was seen preferentially through the ventricularis layer in the cusp (collagen scaffold) and the adventitia in the artery (elastin scaffold). The cells also appeared to have an affinity for the pore spaces in the collagen scaffolds and the spaces between the fibers in the elastin scaffolds. No differences were observed in cell filtration patterns between the non-treated scaffolds implanted in a diabetic environment and the non-treated scaffolds implanted in a control environment. Meanwhile, PGG-treatment of the scaffolds slightly reduced, but did not inhibit, cellular infiltration.

Next, immunohistochemical staining for vimentin, an antibody used for detecting fibroblasts, was performed to determine if fibroblasts were present in the non-treated and PGG-treated collagen and elastin scaffolds, which can indicate the level of remodeling taking place in the implanted scaffolds. The presence of vimentin, and thus the presence of fibroblasts, was indicated by cells stained a dark, brown color. As shown in FIGS. 14 and 15, the non-treated collagen and elastin scaffolds contained numerous fibroblasts. Meanwhile, the PGG-treated collagen and elastin scaffolds also showed the presence of fibroblasts. The presence of the fibroblasts on the PGG-treated scaffolds indicates that treating the scaffolds with PGG still allows for scaffold degradation and tissue remodeling by host fibroblasts.

Immunohistochemical staining for CD8 was then performed to detect the presence of T-lymphocytes in the scaffolds. As shown in FIGS. 14 and 15, a few T-lymphocytes were present, as indicated by the dark brown color, although they were constrained to the edges of the scaffolds. The collagen and elastin scaffolds in diabetic environments appeared to have a greater T-lymphocyte response in the non-treated scaffolds compared to the control non-treated scaffolds. Meanwhile, PGG-treatment of scaffolds appeared to discourage T-lymphocyte infiltration, although it was not completely inhibited.

Lastly, immunohistochemical staining for CD68, a glycoprotein that is a marker for macrophages, was also performed to determine the level of macrophage infiltration in the untreated and PGG-treated collagen and elastin scaffolds. The presence of CD68 marker, and thus the presence of macrophages, was indicated by cells stained a dark, brown color. As shown in FIGS. 14 and 15, the non-treated collagen and elastin scaffolds contained numerous macrophages. Further, more macrophages were present in the diabetic non-treated scaffolds than the control non-treated scaffolds. Meanwhile, the PGG-treated collagen and elastin scaffolds showed a decrease in the amount of cells stained a brown color, indicating that any macrophages present were present in a reduced amount. Based on these results, treating the collagen and elastin scaffolds with PGG prevented the inflammatory response seen in untreated collagen and elastin scaffolds implanted in a diabetic environment, suggesting that PGG might discourage the macrophage inflammatory response of the host to the scaffolds.

Example 6

Figure 16:
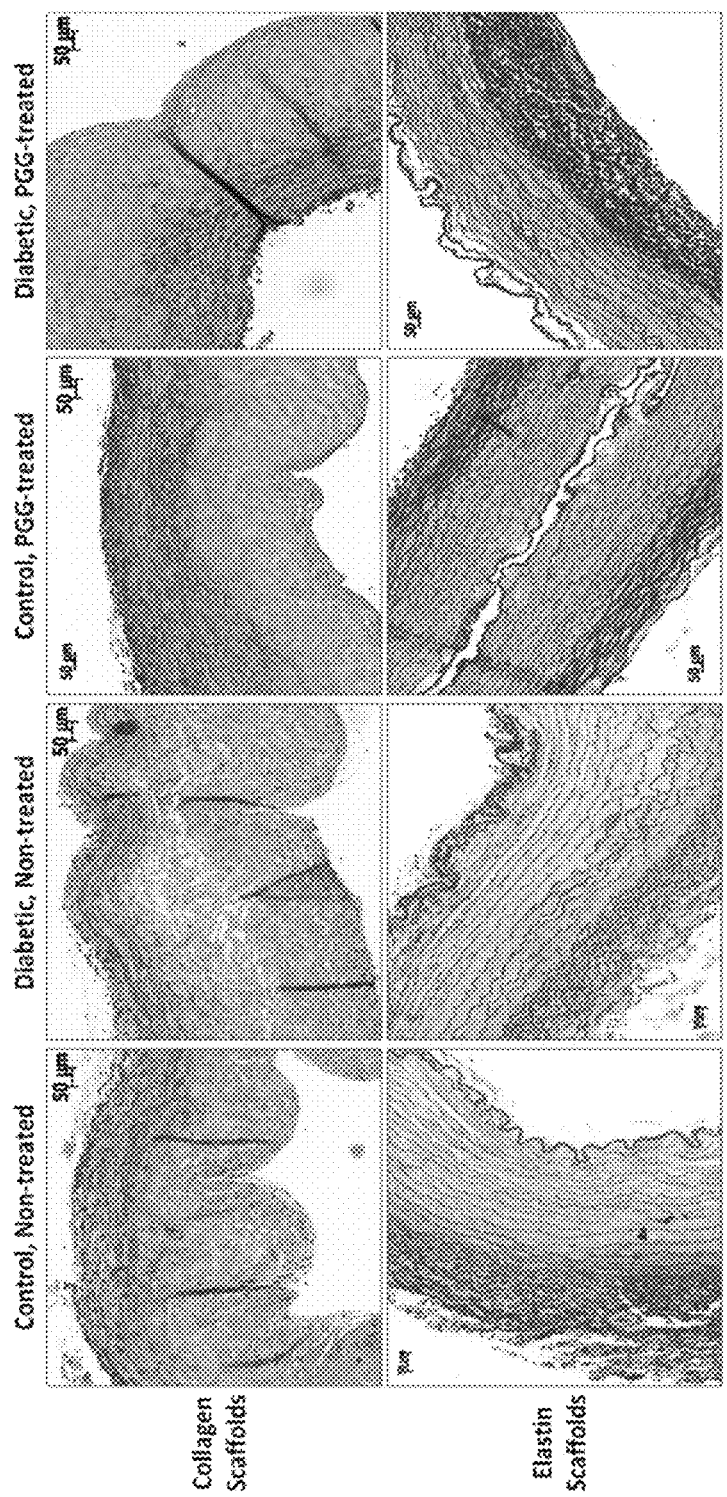
FIG. 16 illustrates extracellular matrix (ECM) remodeling of non-treated and PGG-treated collagen and elastin scaffolds after subdermal implantation in control and diabetic environments.

Next, in Example 6, the amount of ECM remodeling of the collagen and elastin scaffolds of Example 1 after implantation was determined through Movat's Pentachrome staining, as shown in FIG. 16. In the stain, yellow indicates collagen, blue indicates glycosaminoglycans, dark purple indicates elastin, and bright red indicates nuclei.

As demonstrated in FIG. 16, non-treated scaffold integrity was slightly compromised, with signs of matrix degradation visible in both the collagen and elastin scaffolds. On the other hand, treatment of the scaffolds with PGG appears to have preserved the structural integrity of the scaffolds in both the control and diabetic environments.

Example 7

In Example 7, matrix metalloproteinases (MMPs), which are involved in matrix remodeling were detected in the collagen and elastin scaffolds of Example 1 after implantation. Proteins were extracted by pulverizing liquid nitrogen-frozen tissue samples and homogenizing them in RIPA extraction buffer (50 mM tris-HCL, pH 7.4, 150 mM NaCl, 1 mM EDTA, 1% Triton X-100, 1% Sodium Deoxycholate, 0.1% SDS, with protease inhibitor cocktail). Protein concentration was determined using a bicinchoninic acid (BCA) protein assay kit. For each sample, 6 micrograms per lane were loaded, alongside pre-stained molecular weight standards. After staining, the MMP clear bands on a dark background were evaluated by densitometry on a FluorChem SP imager and using the Alpha EaseFC software, version 4.1.0, by Alpha Innotech Corporation (Protein Simple, Santa Clara, Calif.) and expressed as relative density units (RDU) normalized to a protein content. Tissue inhibitors of MMPs (TIMP) levels were measured in the same protein extracts using a rat cytokine array panel (Proteome Profiler Antibody Array Panel A, R&D Systems, Minneapolis, Minn.).

Figure 17:
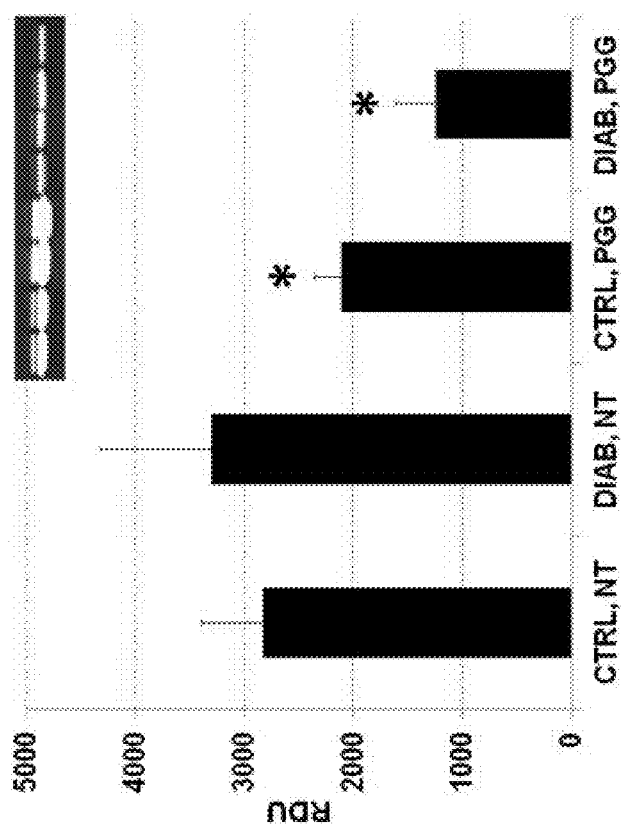
FIG. 17 compares the levels of matrix metalloproteinase (MMP) activity in relative density units (RDU) of non-treated and PGG-treated collagen scaffolds after subdermal implantation in control and diabetic environments.
Figure 18:
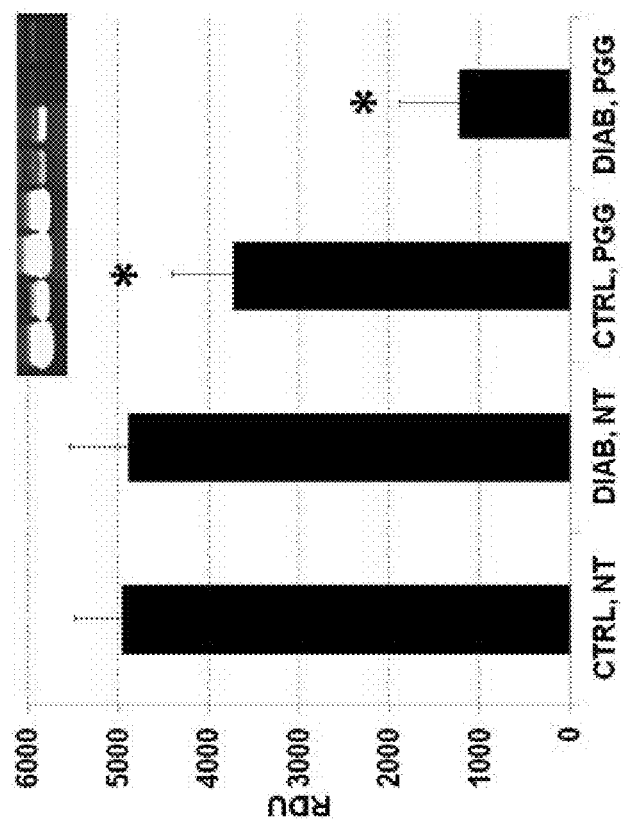
FIG. 18 compares the levels of matrix metalloproteinase activity in relative density units (RDU) of non-treated and PGG-treated elastin scaffolds after subdermal implantation in control and diabetic environments.

The MMP results for the collagen scaffolds are shown in FIG. 17, and the MMP results for the elastin scaffolds are shown in FIG. 18. The results show higher MMP activities in diabetic versus non-treated scaffolds, as well as significantly reduced protease levels in PGG-treated scaffolds. The highest reduction in MMP activity was observed in the PGG-treated scaffold samples in a diabetic environment. Generally, MMP levels were about 50% lower in PGG-treated scaffolds in either a control or diabetic environment, indicating that the remodeling process was decelerated, which would allow for prolonged scaffold retention, which is an essential characteristic for cardiovascular tissue replacement. TIMP levels were highest in the non-treated scaffolds implanted in a control environment (0.27 RDU/mg wet weight) and lowest in PGG-treated scaffolds in a diabetic environment (0.19 RDU/mg wet weight). These results indicate that PGG might prevent the further disorganization of matrix components, reducing the infiltration of inflammatory cells and the synthesis of matrix proteases, which play a significant role in elastin and collagen calcification.

Example 8

Next, in Example 8, the collagen and elastin scaffolds of Example 1 were stained with Alizarin Red to determine if calcium deposits were present, as calcification of implanted tissues is a concern, particularly in diabetic patients. Calcium content was analyzed in tissue protein extracts using a QuantiChrom Calcium Assay Kit (BioAssay Systems, Hayward, Calif.).

Figure 19:
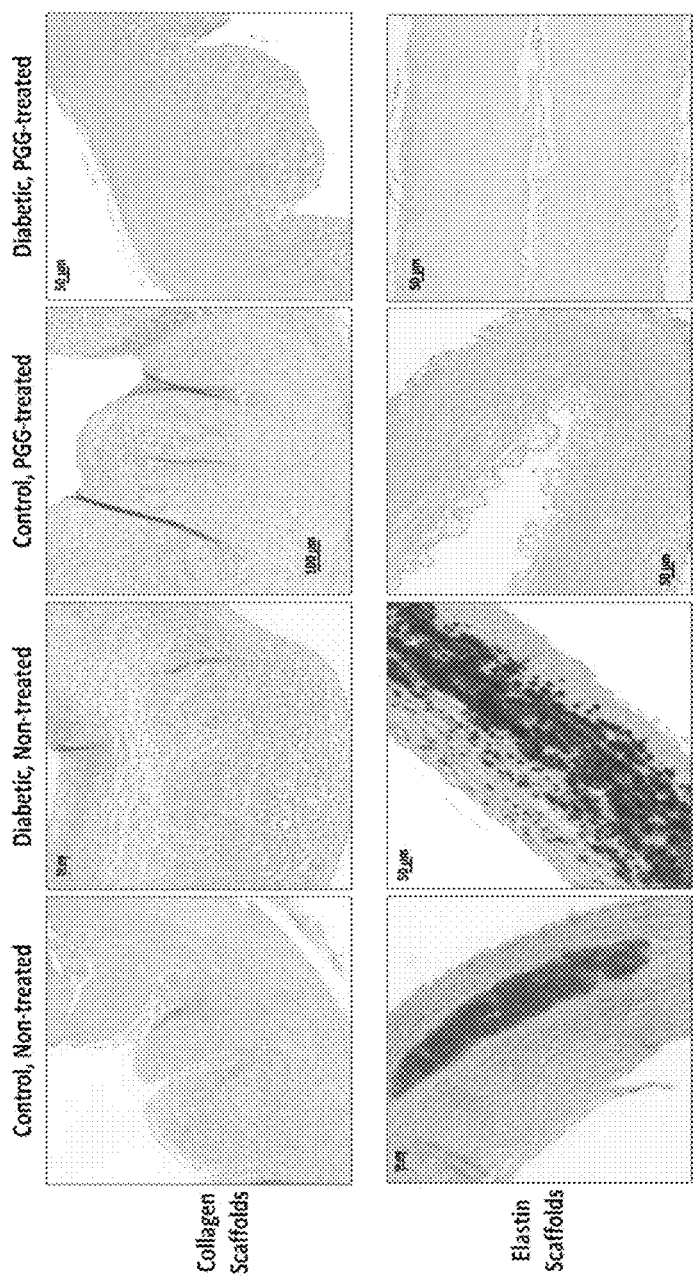
FIG. 19 compares the level of calcification in non-treated and PGG-treated collagen and elastin scaffolds via Alizarin Red histology staining.

As shown in FIG. 19, there was no accumulation of calcium in any of the collagen scaffolds irrespective of diabetic status. Elastin scaffolds, however, calcified significantly after being implanted in either a control or diabetic environment, as shown by the dark red staining. This was equal to 17 micrograms of calcium per milligram of dry weight in the diabetic environment. However, there was no calcification of the elastin scaffolds when treated with PGG in either the control or diabetic environment.

Figure 20:
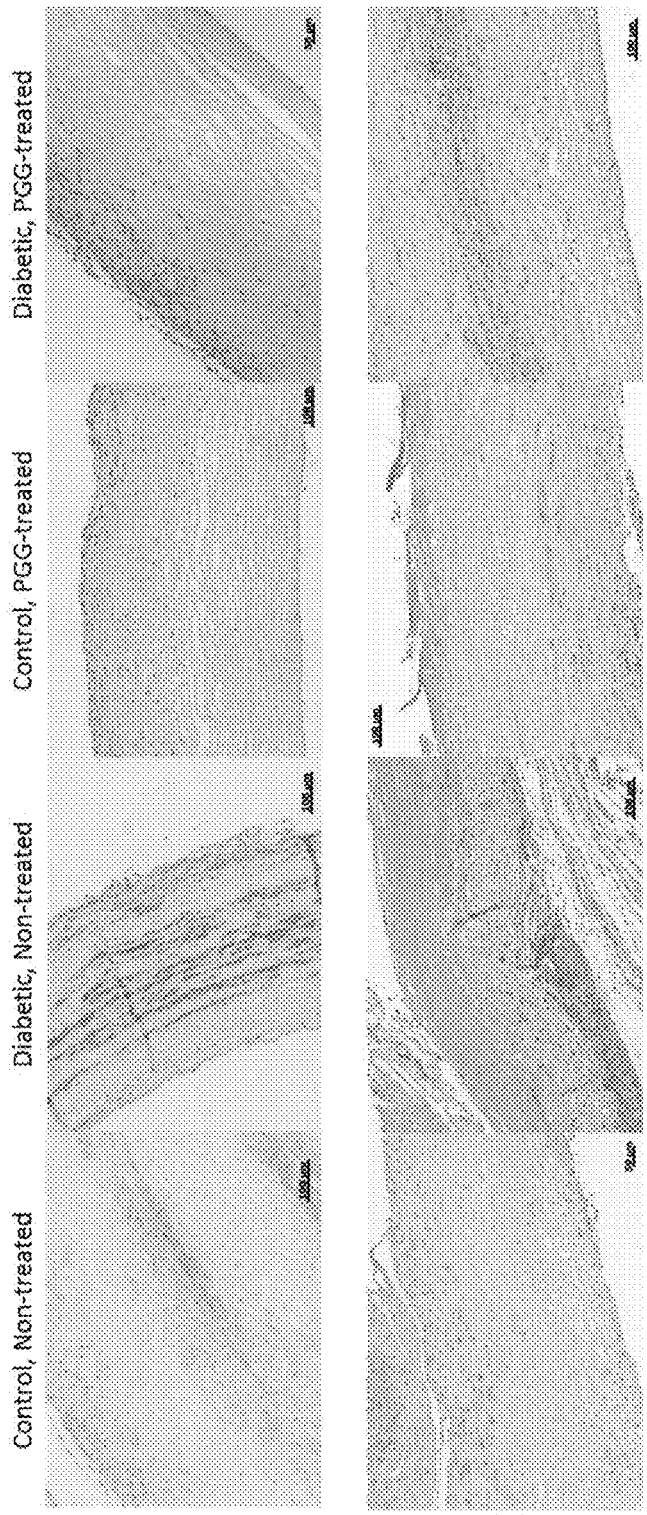
FIG. 20 illustrates the results of staining for osteopontin (A) and alkaline phosphatase (B) in non-treated and PGG-treated elastin scaffolds after subdermal implantation in control and diabetic environments.

Because the elastin scaffolds of Example 1 were prone to calcification when left untreated, the elastin scaffolds were stained with two osteogenic markers as shown in FIG. 20. The scaffolds of row A were stained for osteopontin, while the scaffolds of row B were stained for alkaline phosphatase. As shown, in the untreated elastin scaffolds in either a control or diabetic environment, both calcification markers are present, while in the PGG-treated elastin scaffolds, both calcification markers are absent, indicating that PGG treatments can be used to prevent calcification in implanted elastin-based scaffolds.

Example 9

Figure 21:
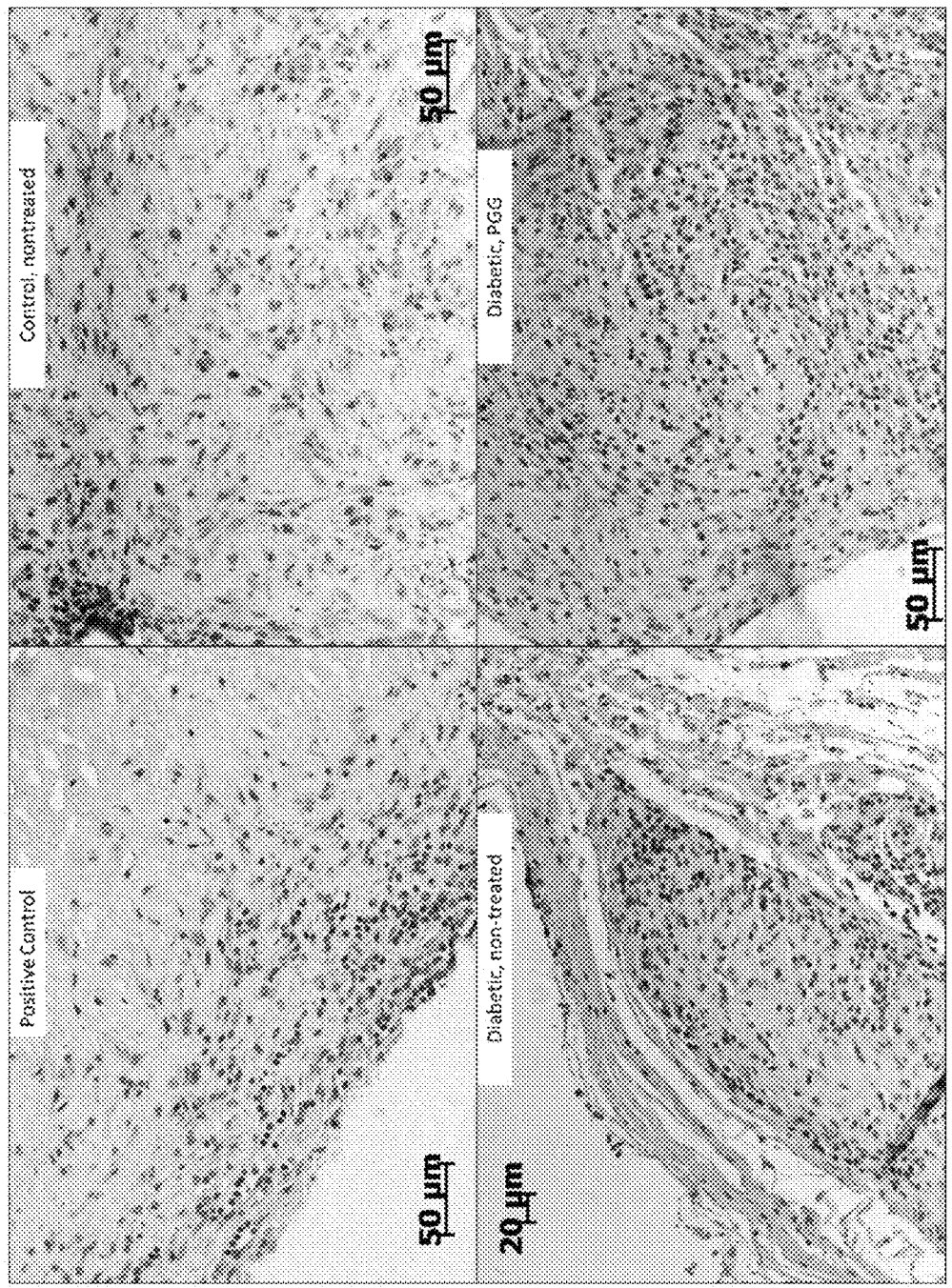
FIG. 21 illustrates the results of CD168, a marker for M2 phenotype macrophages, staining of non-treated and PGG-treated collagen scaffolds after subdermal implantation in control and diabetic environments.

Lastly, in Example 9, immunohistochemical staining of the collagen scaffolds of Example 1 for CD168 was conducted. CD168 is a marker for M2 phenotype macrophages, which are known to be responsible for constructive remodeling and a regenerative type response. M1 phenotype macrophages, on the other hand, are associated with classical inflammation and destructive degradation. As indicated in FIG. 21, the presence of the dark brown color indicates the presence of M2 phenotype macrophages in both the diabetic and control environments, even when the scaffolds were treated with PGG. Thus, this shows that PGG does not inhibit the remodeling associated with M2 phenotype macrophages, and thus does not inhibit tissue regeneration.

Example 10

Figure 22:
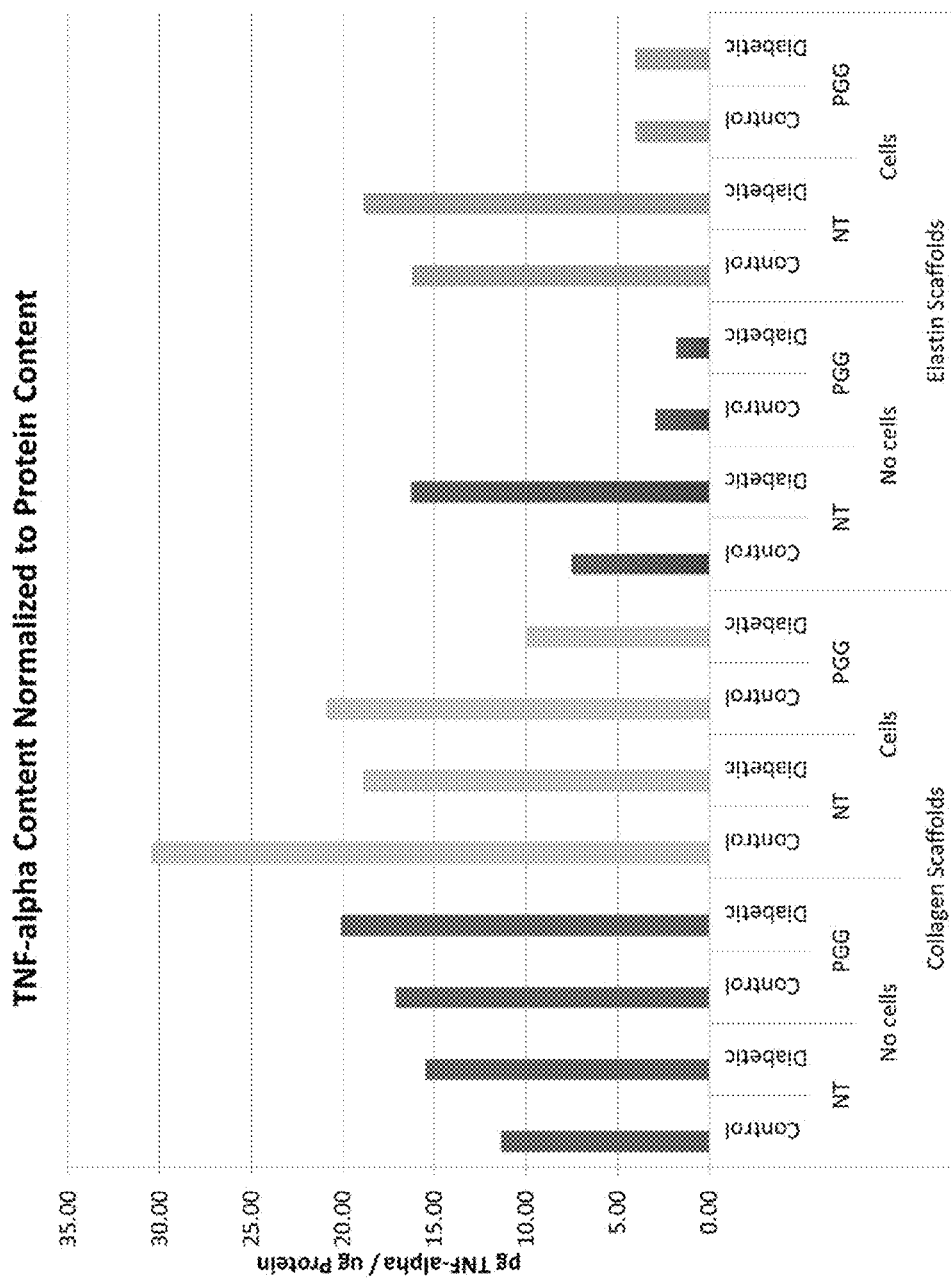
FIG. 22 illustrates the levels of TNF-alpha in non-treated and treated collagen and elastin scaffolds after subdermal implantation in control and diabetic environments.

In Example 10, the collagen and elastin scaffolds of Example 1 were analyzed by running an ELISA for TNF-alpha, a pro-inflammatory cytokine. The amount of TNF-alpha is shown in picograms per micrograms of protein. The results are shown in FIG. 22. Generally, higher amounts of TNF-alpha are associated with diabetic environments. However, scaffolds treated with PGG shows lower amounts of TNF-alpha, indicated that treating scaffolds with PGG can reduce the inflammatory response.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method for rendering an implant resistant to diabetes comprising applying a phenolic compound to the implant by immersing the implant in a treatment solution containing a carrier and the phenolic compound, wherein the phenolic compound is present in the treatment solution at a concentration ranging from about 0.0001 w/v % to about 10 w/v %, wherein the phenolic compound comprises a hydrophobic core and at least one phenolic group joined to the hydrophobic core, further wherein the phenolic compound is pentagalloylglucose and the solution has a pH between about 4 and about 9, wherein the phenolic compound inhibits binding of advanced glycation end products to the implant.

2. The method of claim 1, further comprising implanting the implant into a subject.

3. The method of claim 1, wherein the implant is implanted into a diabetic environment.

4. The method of claim 1, wherein the phenolic compound inhibits degradation of the implant.

5. A composition for rendering an implant resistant to diabetes comprising:
between about 00001 w/v % and about 10 w/v % of a phenolic compound, the phenolic compound comprising a hydrophobic core and at least one phenolic group joined to the hydrophobic core; further wherein the phenolic compound is pentagalloylglucose, wherein the phenolic compound inhibits binding of advanced glycation end products to the implant; and
a carrier;
wherein the composition has a pH between about 4 and about 9.

6. The composition of claim 5, wherein the phenolic compound comprises one or more double bonds.

7. The composition of claim 5, wherein the composition has a pH of between about 5.5 and about 7.4.

8. The composition of claim 5, wherein the composition comprises less than about 5% free gallic acid residue.

9. An implant that is resistant to diabetes, the implant comprising a scaffold treated with a solution comprising about 0.0001 w/v % and about 10 w/v % of a phenolic compound, the phenolic compound comprising a hydrophobic core and at least one phenolic group joined to the hydrophobic core, further wherein the phenolic compound is pentagalloylglucose, wherein the phenolic compound inhibits binding of advanced glycation end products to the implant.

10. The implant of claim 9, wherein the implant is a collagen-based scaffold or an elastin-based scaffold.

11. The implant of claim 9, wherein the implant is a replacement heart valve.

12. The implant of claim 11, wherein the implant is a replacement blood vessel.

13. The implant of claim 12, wherein the replacement blood vessel is a decellularized artery.

14. The implant of claim 9, wherein the phenolic compound comprises one or more double bonds.

* * * * *